(12) United States Patent
Choi et al.

(10) Patent No.: US 12,145,953 B2
(45) Date of Patent: Nov. 19, 2024

(54) EMITTING COMPOUND AND ORGANIC LIGHT EMITTING DEVICE INCLUDING THE SAME

(71) Applicant: LG DISPLAY CO., LTD., Seoul (KR)

(72) Inventors: Su-Na Choi, Paju-si (KR); In-Bum Song, Paju-si (KR); Jeong-Dae Seo, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 733 days.

(21) Appl. No.: 17/374,362

(22) Filed: Jul. 13, 2021

(65) Prior Publication Data

US 2022/0204532 A1 Jun. 30, 2022

(30) Foreign Application Priority Data

Dec. 29, 2020 (KR) .................. 10-2020-0186020

(51) Int. Cl.
*C07F 5/02* (2006.01)
*C07D 493/00* (2006.01)
*H01L 51/00* (2006.01)
*H10K 85/60* (2023.01)
*H10K 101/00* (2023.01)

(52) U.S. Cl.
CPC ............ *C07F 5/027* (2013.01); *C07D 493/00* (2013.01); *H10K 85/626* (2023.02); *H10K 85/636* (2023.02); *H10K 85/6574* (2023.02); *H10K 2101/90* (2023.02)

(58) Field of Classification Search
None
See application file for complete search history.

(56) References Cited

U.S. PATENT DOCUMENTS

2020/0172558 A1* 6/2020 Joo .................. H10K 85/6572

FOREIGN PATENT DOCUMENTS

| CN | 111253421 A | 6/2020 |
|---|---|---|
| CN | 112086568 A | 12/2020 |
| CN | 112592362 A | 4/2021 |
| CN | 113812015 A | 12/2021 |
| CN | 113841262 A | 12/2021 |
| CN | 113853377 A | 12/2021 |
| CN | 114695761 A | 7/2022 |
| JP | 2004018447 A * | 1/2004 |

(Continued)

*Primary Examiner* — Tae H Yoon
(74) *Attorney, Agent, or Firm* — Birch, Stewart, Kolasch & Birch, LLP

(57) ABSTRACT

The present disclosure relates to an emitting compound and organic light emitting device including the same, and more specifically, relates to an emitting compound of following and an organic light emitting diode and an organic light emitting device each including the emitting compound.

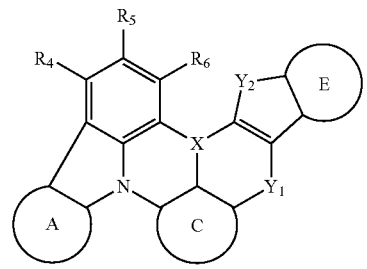

13 Claims, 4 Drawing Sheets

(56) References Cited

FOREIGN PATENT DOCUMENTS

| JP | 5724588 | * | 5/2015 |
|----|---------|---|--------|
| KR | 10-2094830 B1 | | 3/2020 |
| TW | 201111474 A | * | 4/2011 |
| WO | WO 2017/188111 A1 | * | 2/2017 |
| WO | WO 2020/111830 A1 | | 6/2020 |

* cited by examiner

EMITTING COMPOUND AND ORGANIC LIGHT EMITTING DEVICE INCLUDING THE SAME

CROSS-REFERENCE TO RELATED APPLICATIONS

The present application claims the benefit of Korean Patent Application No. 10-2020-0186020 filed in the Republic of Korea on Dec. 29, 2020, which is hereby incorporated by reference in its entirety.

BACKGROUND OF THE INVENTION

Field of Technology

The present disclosure relates to an emitting compound, and more specifically, to an emitting compound having high emitting efficiency and lifespan and an organic light emitting device including the same.

Discussion of the Background Art

As requests for a flat panel display device having a small occupied area have been increased, an organic light emitting display device including an organic light emitting diode (OLED) has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color sense.

For example, the organic light emitting display device can include a red pixel region, a green pixel region and a blue pixel region, and the OLED can be formed in each of the red, green and blue pixel regions.

However, the OLED in the blue pixel does not provide sufficient emitting efficiency and lifespan such that the organic light emitting display device has a limitation in the emitting efficiency and the lifespan.

SUMMARY OF THE INVENTION

The present disclosure is directed to an emitting compound and an organic light emitting device including the emitting compound that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure is an emitting compound represented by Formula 1:

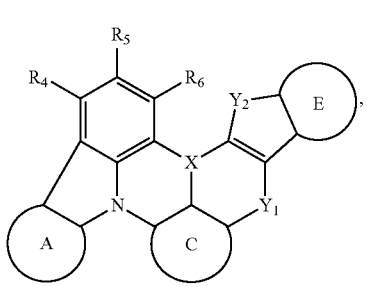

[Formula 1]

wherein X is one of B, P=O and P=S, wherein $Y_1$ is selected from the group consisting of $NR_1$, $C(R_2)_2$, O, S, Se and $Si(R_3)_2$, and $Y_2$ is O or S, wherein each of $R_1$ to $R_6$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, and wherein each of A, E and C rings is independently selected from the group consisting of substituted or unsubstituted six-membered cycloalkyl ring, substituted or unsubstituted six-membered aromatic ring and substituted or unsubstituted six-membered heteroaromatic ring.

Another aspect of the present disclosure is an organic light emitting device comprising a substrate; and an organic light emitting diode positioned on the substrate and including a first electrode; a second electrode facing the first electrode; and a first emitting material layer including a first compound and positioned between the first and second electrodes, wherein the first compound is the above emitting compound.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION OF THE EMBODIMENTS

Reference will now be made in detail to some of the examples and preferred embodiments, which are illustrated in the accompanying drawings.

Figure 1:
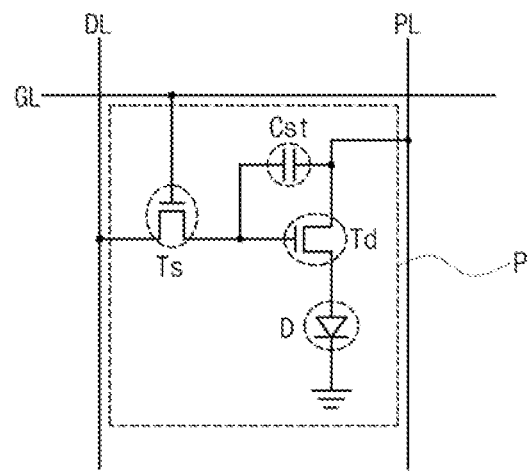
FIG. 1 is a schematic circuit diagram illustrating an organic light emitting display device according to one or more embodiments of the present disclosure.

FIG. 1 is a schematic circuit diagram illustrating an organic light emitting display device of the present disclosure.

As illustrated in FIG. 1, a gate line GL and a data line DL, which cross each other to define a pixel (pixel region) P, and a power line PL are formed in an organic light display device. A switching thin film transistor (TFT) Ts, a driving thin film transistor (TFT) Td, a storage capacitor Cst and an OLED D are formed in the pixel region P. The pixel region P can include a red pixel, a green pixel and a blue pixel.

The switching thin film transistor Ts is connected to the gate line GL and the data line DL, and the driving thin film transistor Td and the storage capacitor Cst are connected between the switching thin film transistor Ts and the power line PL. The OLED D is connected to the driving thin film transistor Td. When the switching thin film transistor Ts is turned on by the gate signal applied through the gate line GL, the data signal applied through the data line DL is applied a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the OLED D through the driving thin film transistor Td. The OLED D emits light having a luminance proportional to the current flowing through the driving thin film transistor Td. In this case, the storage capacitor Cst is charged with a voltage proportional to the data signal so that the voltage of the gate electrode in the driving thin film transistor Td is kept constant during one frame. Therefore, the organic light emitting display device can display a desired image.

Figure 2:
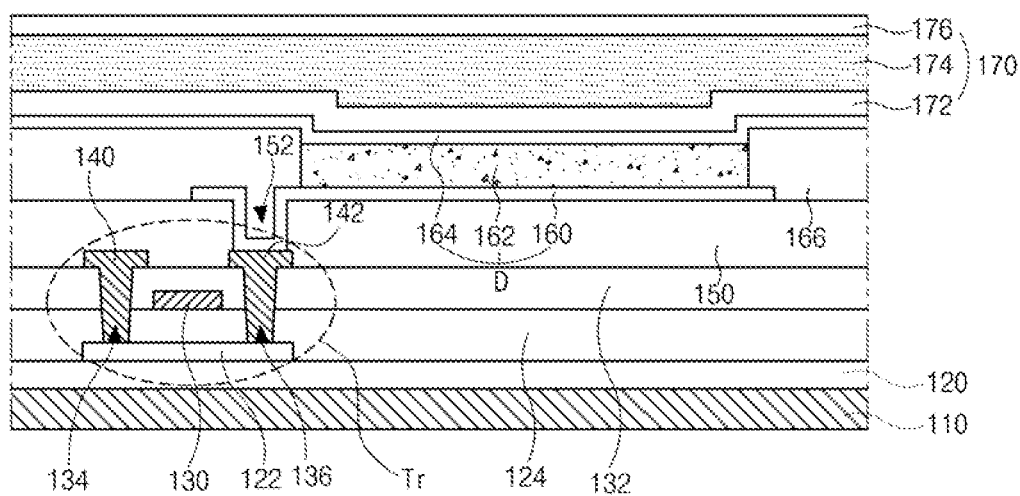
FIG. 2 is a schematic cross-sectional view illustrating an organic light emitting display device according to a first embodiment of the present disclosure.

FIG. 2 is a schematic cross-sectional view illustrating an organic light emitting display device according to a first embodiment of the present disclosure. All components of the organic light emitting display device according to all embodiments of the present disclosure are operatively coupled and configured.

As illustrated in FIG. 2, an organic light emitting display device 100 includes a substrate 110, a TFT Tr and an OLED D connected to the TFT Tr. For example, the organic light emitting display device 100 can include a red pixel, a green pixel and a blue pixel, and the OLED D can be formed in each of the red, green and blue pixels. Namely, the OLEDs D emitting red light, green light and blue light can be provided in the red, green and blue pixels, respectively.

The substrate 110 can be a glass substrate or a flexible substrate. For example, the flexible substrate can be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 120 is formed on the substrate, and the TFT Tr is formed on the buffer layer 120. The buffer layer 120 can be omitted.

A semiconductor layer 122 is formed on the buffer layer 120. The semiconductor layer 122 can include an oxide semiconductor material or polycrystalline silicon.

When the semiconductor layer 122 includes the oxide semiconductor material, a light-shielding pattern can be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities can be doped into both sides of the semiconductor layer 122.

A gate insulating layer 124 is formed on the semiconductor layer 122. The gate insulating layer 124 can be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 can be patterned to have the same shape as the gate electrode 130.

An interlayer insulating layer 132, which is formed of an insulating material, is formed on the gate electrode 130. The interlayer insulating layer 132 can be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element. Namely, the TFT Tr can correspond to the driving TFT Td (of FIG. 1).

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode can be positioned under the semiconductor layer, and the source and drain electrodes can be positioned over the semiconductor layer such that the TFT Tr can have an inverted staggered structure. In this instance, the semiconductor layer can include amorphous silicon.

The gate line and the data line cross each other to define the pixel, and the switching TFT is formed to be connected to the gate and data lines. The switching TFT is connected to the TFT Tr as the driving element.

In addition, the power line, which can be formed to be parallel to and spaced apart from one of the gate and data lines, and the storage capacitor for maintaining the voltage of the gate electrode of the TFT Tr in one frame can be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel and on the passivation layer 150. The first electrode 160 can be an anode and can be formed of a conductive material, e.g., a transparent conductive oxide (TCO), having a relatively high work function. For example, the first electrode 160 can be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 160 can have a single-layered structure of the transparent conductive material layer. When the Organic light emitting display device 100 is operated in a top-emission type, a reflection electrode or a reflection layer can be formed under the first electrode 160. For example, the reflection electrode or the reflection layer can be formed of silver (Ag) or aluminum-palladium-copper (APC) alloy. In this instance, the first electrode 160 can have a triple-layered structure of ITO/Ag/ITO or ITO/APC/ITO.

A bank layer 166 is formed on the passivation layer 150 to cover an edge of the first electrode 160. Namely, the bank layer 166 is positioned at a boundary of the pixel and exposes a center of the first electrode 160 in the pixel.

An organic emitting layer 162 is formed on the first electrode 160. The organic emitting layer 162 can have a single-layered structure of an emitting material layer including an emitting material. To increase an emitting efficiency of the OLED D and/or the organic light emitting display device 100, the organic emitting layer 162 can have a multi-layered structure.

The organic emitting layer 162 is separated in each of the red, green and blue pixels. As illustrated below, the organic emitting layer 162 in the blue pixel includes an emitting compound of Formula 1 such that the emitting efficiency and the lifespan of the OLED D in the blue pixel are improved.

A second electrode 164 is formed over the substrate 110 where the organic emitting layer 162 is formed. The second electrode 164 covers an entire surface of the display area and can be formed of a conductive material having a relatively low work function to serve as a cathode. For example, the second electrode 164 can be formed of aluminum (Al), magnesium (Mg), calcium (Ca), silver (Ag) or their alloy or combination. In the top-emission type organic light emitting display device 100, the second electrode 164 can have a thin profile (small thickness) to provide a light transmittance property (or a semi-transmittance property).

The first electrode 160, the organic emitting layer 162 and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 can be omitted.

The organic light emitting display device 100 can further include a polarization plate for reducing an ambient light reflection. For example, the polarization plate can be a circular polarization plate. In the bottom-emission type organic light emitting display device 100, the polarization plate can be disposed under the substrate 110. In the top-emission type organic light emitting display device 100, the polarization plate can be disposed on or over the encapsulation film 170.

In addition, in the top-emission type organic light emitting display device 100, a cover window can be attached to the encapsulation film 170 or the polarization plate. In this instance, the substrate 110 and the cover window have a flexible property such that a flexible organic light emitting display device can be provided.

Figure 3:
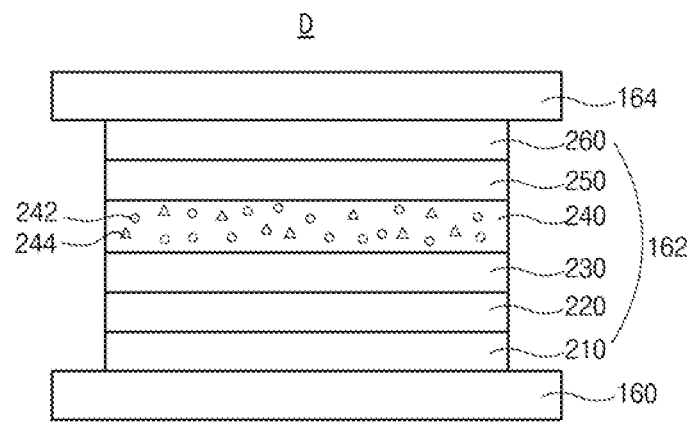
FIG. 3 is a schematic cross-sectional view illustrating an OLED having a single emitting part for the organic light emitting display device according to the first embodiment of the present disclosure.

FIG. 3 is a schematic cross-sectional view illustrating an OLED having a single emitting unit for the organic light emitting display device according to the first embodiment of the present disclosure.

As illustrated in FIG. 3, the OLED D includes the first and second electrodes 160 and 164, which face each other, and the organic emitting layer 162 therebetween. The organic emitting layer 162 includes an emitting material layer (EML) 240 between the first and second electrodes 160 and 164. The organic light emitting display device 100 (of FIG. 2) can include a red pixel, a green pixel and a blue pixel, and the OLED D can be positioned in the blue pixel.

One of the first and second electrodes 160 and 164 is an anode, and the other one of the first and second electrodes 160 and 164 is cathode. In addition, one of the first and second electrodes 160 and 164 can be a transparent (or a semi-transparent) electrode, and the other one of the first and second electrodes 160 and 164 can be a reflection electrode.

The organic emitting layer 162 can further include an electron blocking layer (EBL) 230 between the first electrode 160 and the EML 240 and a hole blocking layer (HBL) 250 between the EML 240 and the second electrode 164.

In addition, the organic emitting layer 162 can further include a hole transporting layer (HTL) 220 between the first electrode 160 and the EBL 230.

Moreover, the organic emitting layer 162 can further include a hole injection layer (HIL) 210 between the first electrode 160 and the HTL 220 and an electron injection layer (EIL) 260 between the second electrode 164 and the HBL 250.

The EML 240 includes an emitting compound 242 as a first compound. The emitting compound is a polycyclic heteroaromatic compound and is represented by Formula 1.

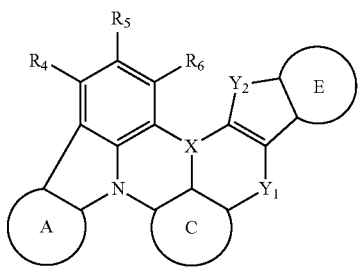

[Formula 1]

In Formula 1, X is one of B, P=O and P=S. $Y_1$ is selected from the group consisting of $NR_1$, $C(R_2)_2$, O, S, Se and $Si(R_3)_2$, and $Y_2$ is O or S. Each of $R_1$ to $R_6$ is independently selected from the group consisting of hydrogen, deuterium (D), C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl.

Each of A, E and C rings is independently selected from the group consisting of substituted or unsubstituted six-membered cycloalkyl ring, substituted or unsubstituted six-membered aromatic ring and substituted or unsubstituted six-membered heteroaromatic ring. In each of the A, E and C rings, hydrogen can be substituted by at least one of D, C1 to C10 alkyl group, C6 to C30 aryl group and C5 to C30 heteroaryl group.

For example, C1 to C10 alkyl group can be selected from the group consisting of methyl, ethyl, and tert-butyl, and C6 to C30 aryl group can be selected from the group consisting of phenyl, naphthyl, and biphenyl. In addition, C6 to C30 arylamine group can be diphenylamine group, and C5 to C30 heteroaryl group can be selected from the group consisting of dibenzofuranyl, dibenzothiophenyl, and carbazoyl. The six-membered cycloalkyl ring can be cyclohexane ring, the six-membered aromatic ring can be benzene ring, and the six-membered heteroaromatic ring can be pyridine ring.

In one embodiment, each of the A and E rings can be unsubstituted or substituted cyclohexane ring, and the C ring can be unsubstituted or substituted benzene ring. Namely, the emitting compound in Formula 1 can be represented by Formula 2-1.

[Formula 2-1]

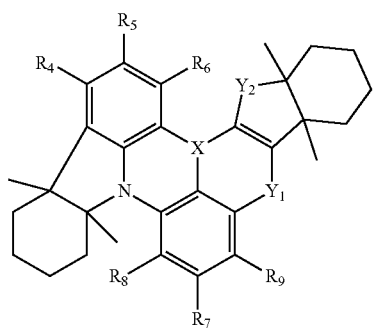

In addition, in Formula 2-1, each of $R_7$, $R_8$, and $R_9$ is independently selected from the group consisting of hydrogen, deuterium, C1 to C10 alkyl group unsubstituted or substituted with deuterium (D), C6 to C30 arylamine group unsubstituted or substituted with D or C1 to C10 alkyl, C6 to C30 aryl group unsubstituted or substituted with D or C1 to C10 alkyl, and C5 to C30 heteroaryl group unsubstituted or substituted with D or C1 to C10 alkyl.

In Formula 2-1, X can be B, and $Y_1$ can be $NR_1$. Namely, the emitting compound in Formula 1 can be represented by Formula 2-2.

[Formula 2-2]

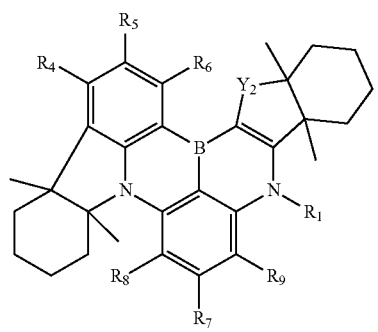

For example, in Formula 2-2, $R_1$ can be C6 to C30 aryl group (e.g., phenyl) substituted with C1 to C10 alkyl (e.g., tert-butyl) or C5 to C30 heteroaryl group (e.g., dibenzofuranyl) substituted with C1 to C10 alkyl (e.g., tert-butyl). In addition, two of $R_4$ to $R_6$ can be hydrogen, and the other of $R_4$ to $R_6$ can be C1 to C10 alkyl group (e.g., tertiary butyl) or C6 to C30 arylamine group (e.g., diphenylamine group) substituted with C1 to C10 alkyl (e.g., tertiary butyl). Further, $R_7$ can be C1 to C10 alkyl group (e.g., tert-butyl), and $R_8$ and $R_9$ can be hydrogen.

Alternatively, in Formula 1, the A ring can be unsubstituted or substituted six-membered heteroaromatic ring, and each of the E and C rings can be unsubstituted or substituted benzene ring. Namely, the emitting compound in Formula 1 can be represented by Formula 2-3.

[Formula 2-3]

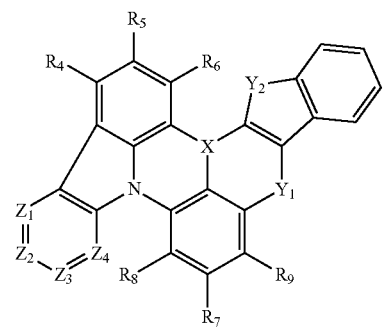

In addition, in Formula 2-3, each of $Z_1$ to $Z_4$ is independently N or $CR_{10}$, and at least one of $Z_1$ to $Z_4$ is N. Each of $R_7$ to $R_{10}$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl.

In Formula 2-3, X can be B, and $Y_1$ can be $NR_1$. Namely, the emitting compound in Formula 1 can be represented by Formula 2-4.

[Formula 2-4]

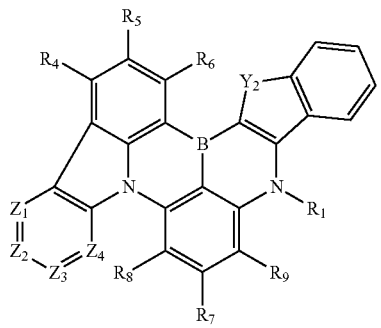

For example, in Formula 2-4, $R_1$ can be C6 to C30 aryl group (e.g., phenyl or biphenyl) or C5 to C30 heteroaryl group (e.g., dibenzofuranyl). In addition, $R_4$ to $R_9$ can be hydrogen, and one of $Z_1$ to $Z_4$ is N.

The emitting compound of the present disclosure as the first compound 242 can be one of compounds in Formula 3.

[Formula 3]

1-1

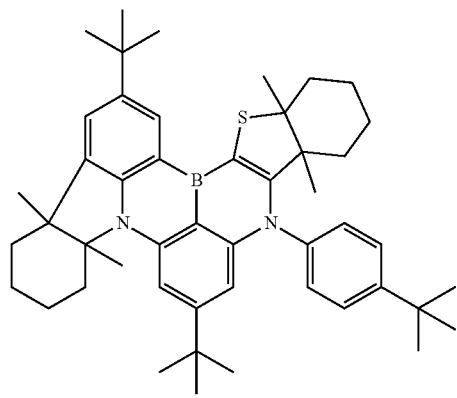

1-2

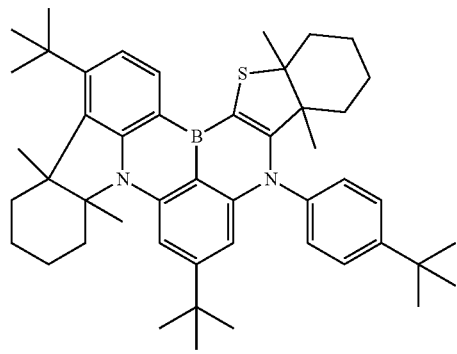

-continued 1-3

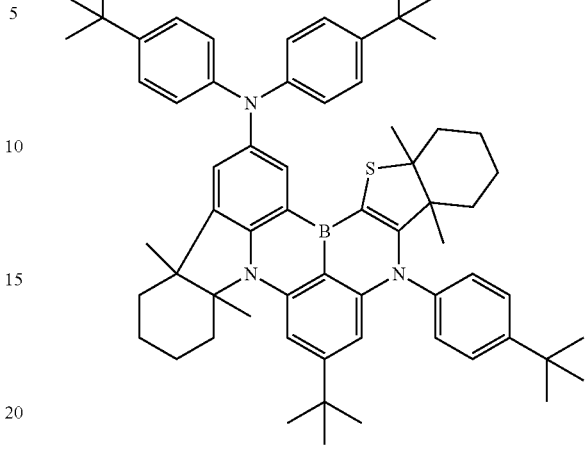

1-4

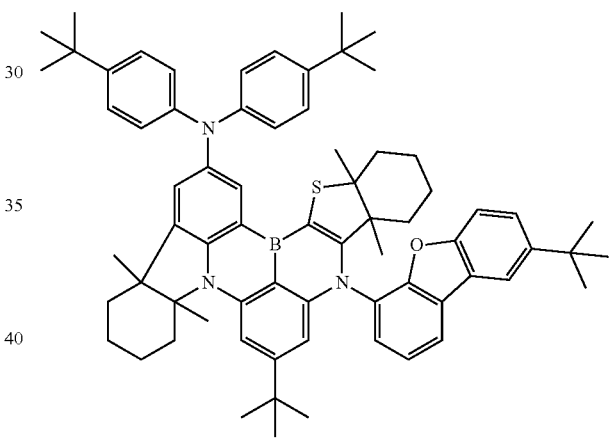

1-5

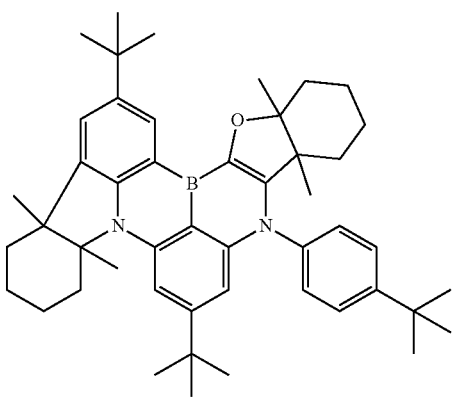

1-6
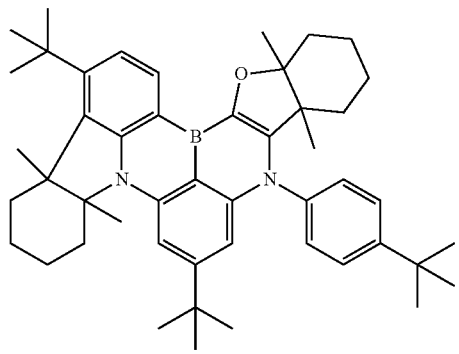
1-7
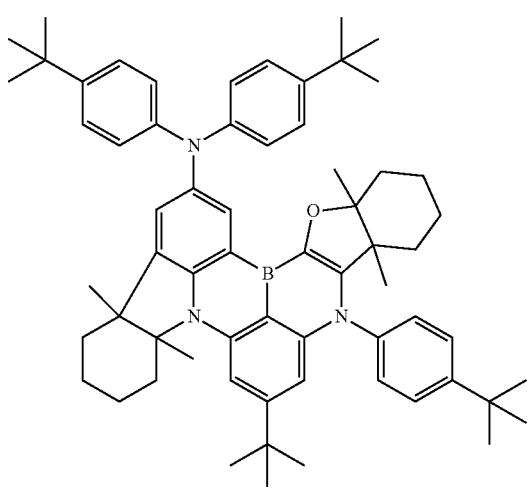
1-8
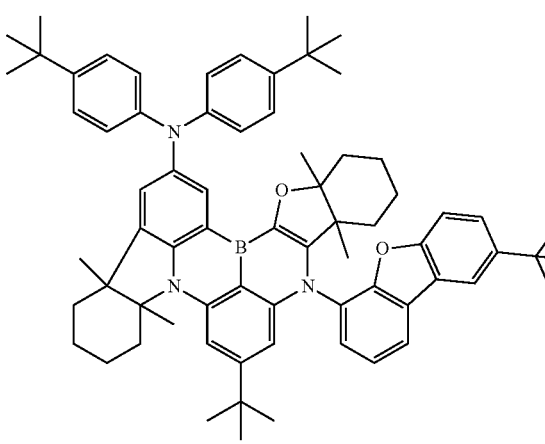
2-1
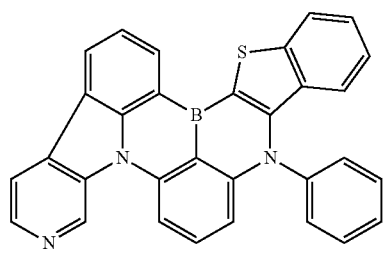
2-2
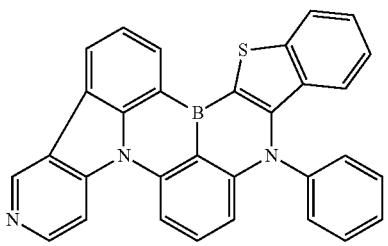
2-3
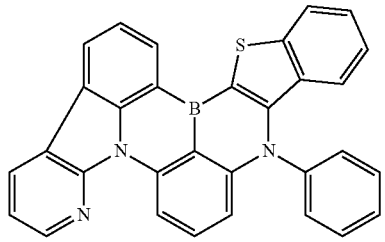
2-4
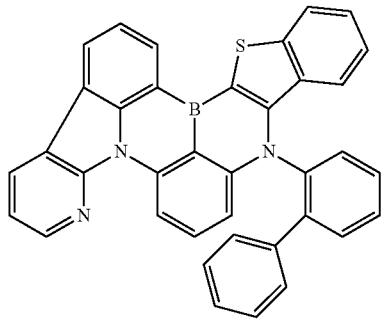
2-5
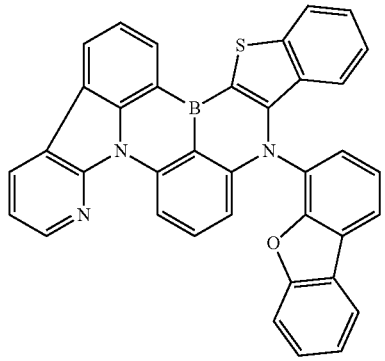
2-6
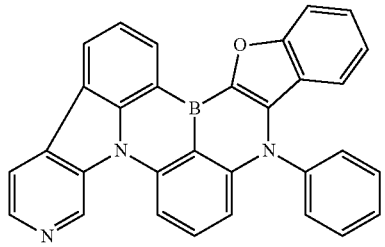

2-7

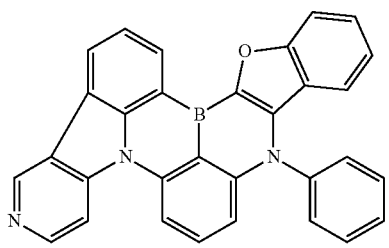

2-8

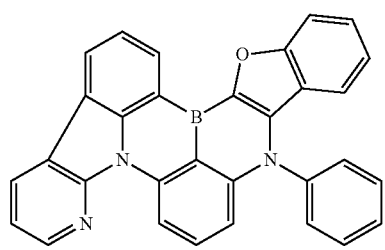

2-9

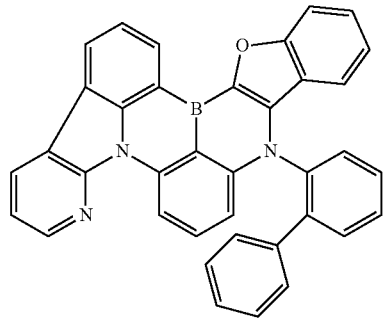

2-10

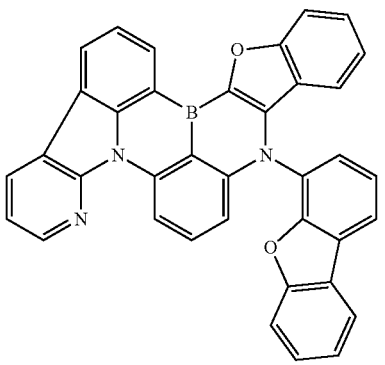

The emitting compound in Formula 1 provides blue emission and is used for the EML 240 in the OLED D. As a result, the lifespan of the OLED D and the organic light emitting display device 100 is significantly increased.

[Synthesis of the Dopant]
1. Synthesis of Compound 1-1
(1) Compound I1-1c

[Reaction Formula 1-1]

In the 500 mL reactor, the compound I1-1a 12.9 g (50 mmol), the compound I1-1b 25.9 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred/refluxed for 5 hours. After completion of the reaction, the resultant was filtered and concentrated. The mixture was separated by column chromatography to obtain 19.2 g of the compound I1-1c. (Yield 52%)

(2) Compound 1-1

2. Synthesis of Compound 1-3

(1) compound I1-3c

[Reaction Formula 1-2]

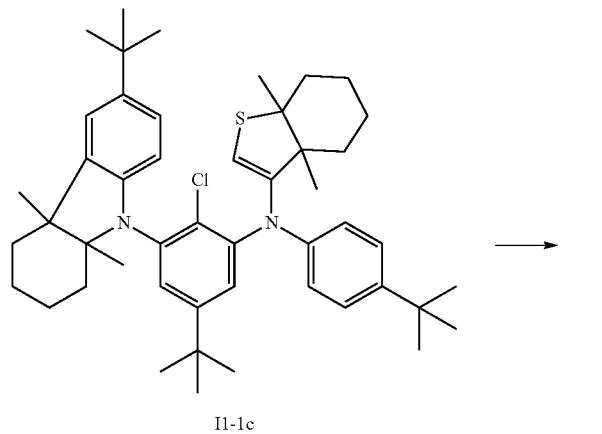

[Reaction Formula 2-1]

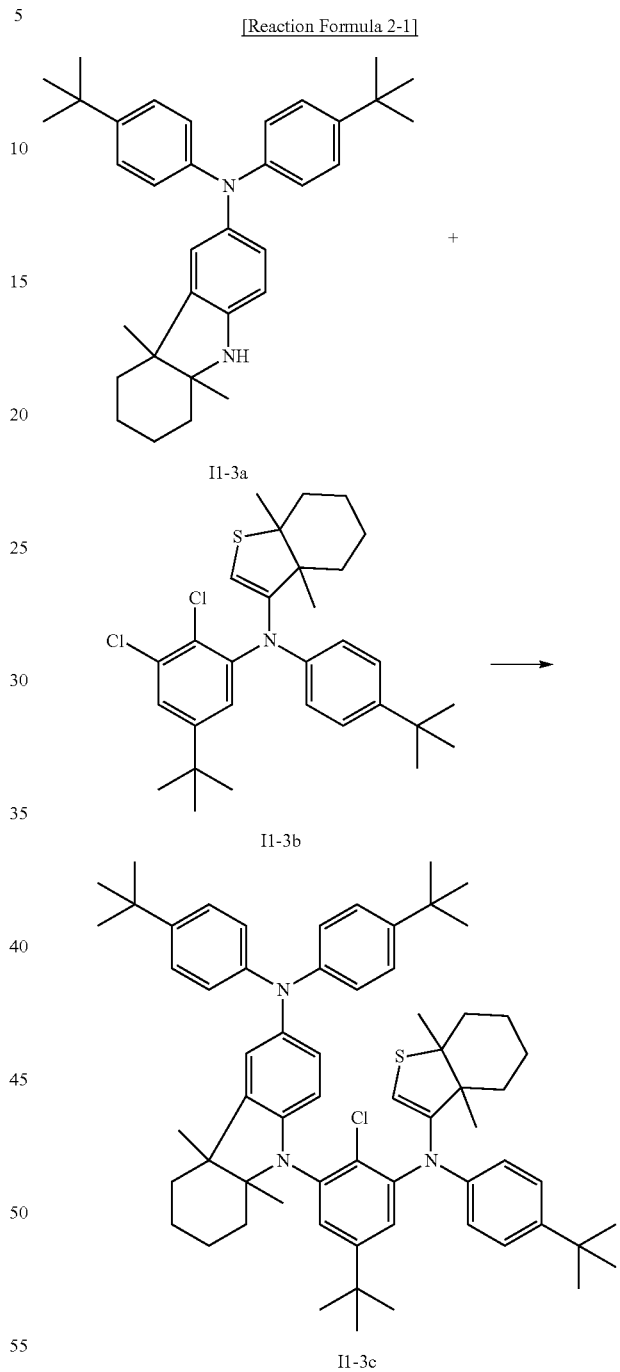

In the 500 mL reactor, the compound I1-1c 9.2 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.3 g of the compound 1-1. (Yield 15%)

In the 500 mL reactor, the compound I1-3a 24.0 g (50 mmol), the compound I1-3b 25.8 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred/refluxed for 5 hours. After the reaction was completed, the resultant was filtered and concentrated. The mixture was separated by column chromatography to obtain 22.1 g of the compound I1-3c. (Yield 46%)

(2) Compound 1-3

3. Synthesis of Compound 1-4

(1) Compound I1-4c

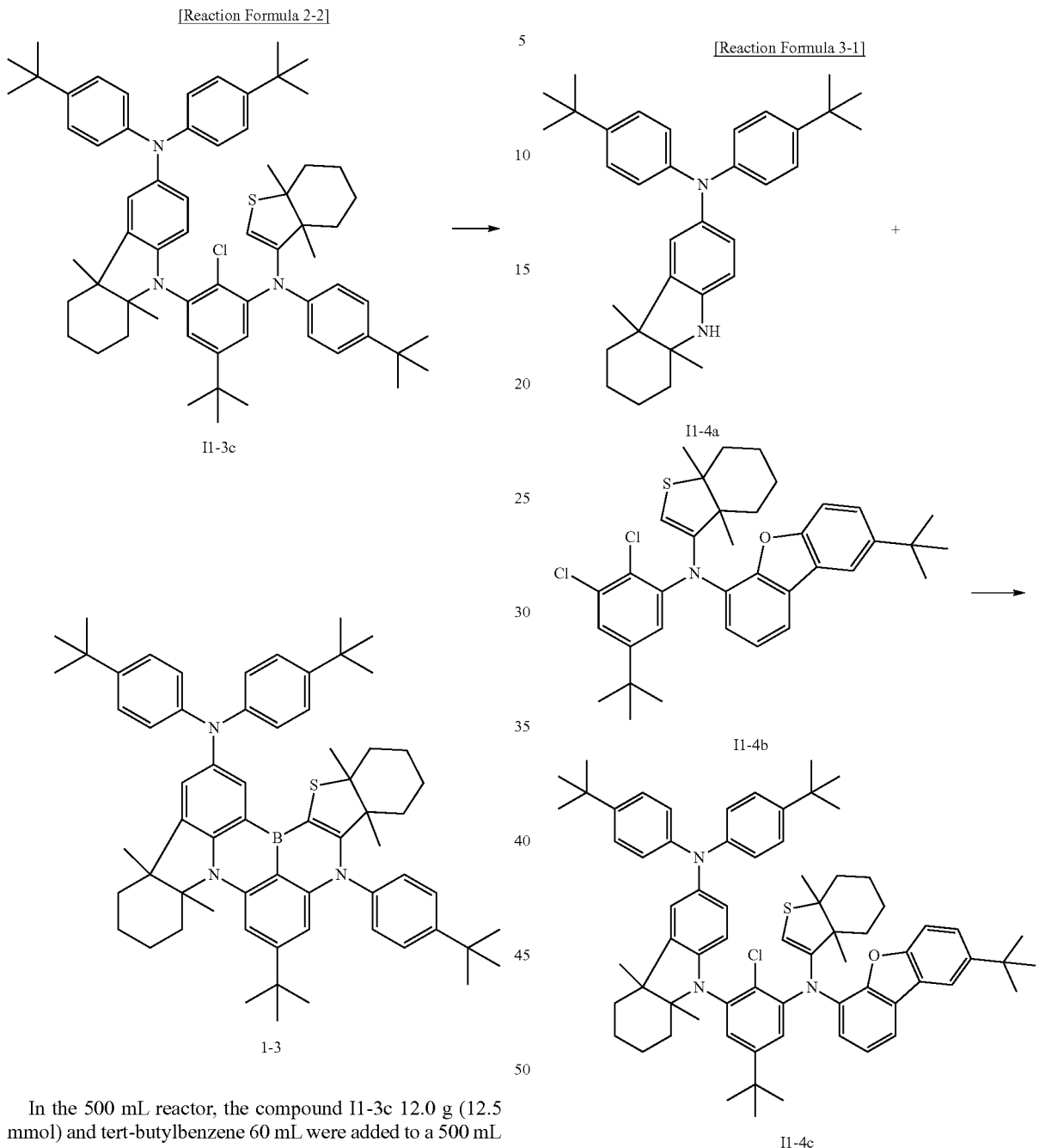

In the 500 mL reactor, the compound I1-3c 12.0 g (12.5 mmol) and tert-butylbenzene 60 mL were added to a 500 mL reactor. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.4 g of the compound 1-3. (Yield 12%)

In the 500 mL reactor, the compound I1-4a 24.0 g (50 mmol), the compound I1-4b 30.3 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred/refluxed for 5 hours. After completion of the reaction, the resultant was filtered and concentrated. The mixture was separated by column chromatography to obtain 25.2 g of the compound I1-4c. (Yield 48%)

(2) Compound 1-4

4. Synthesis of Compound 1-6

(1) Compound I1-6c

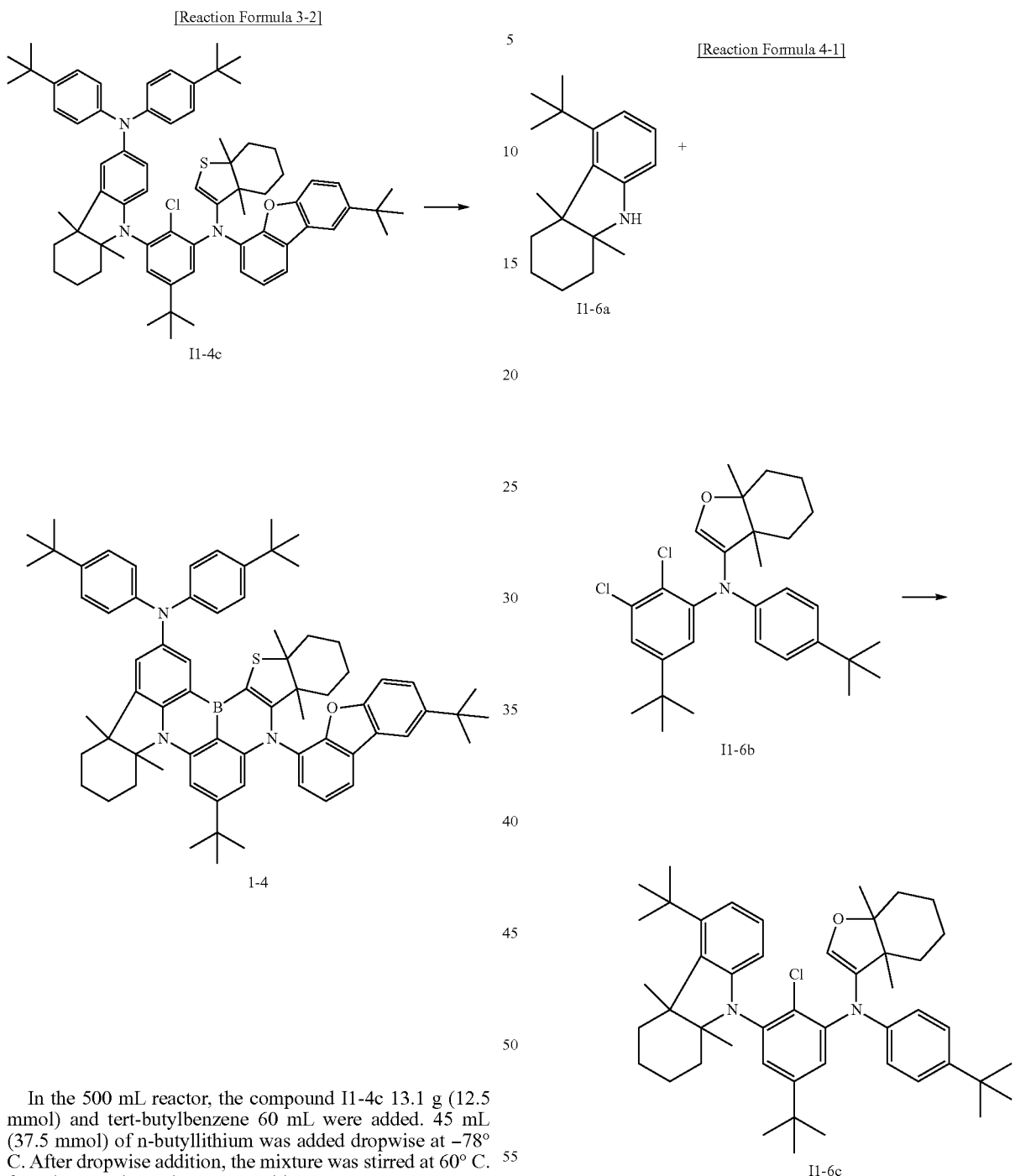

[Reaction Formula 3-2]

I1-4c 1-4

[Reaction Formula 4-1]

I1-6a

I1-6b

I1-6c

In the 500 mL reactor, the compound I1-4c 13.1 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.8 g of the compound 1-4. (Yield 14%)

In the 500 mL reactor, the compound I1-6a 12.9 g (50 mmol), the compound I1-6b 23.3 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred/refluxed for 5 hours. After completion of the reaction, the resultant was filtered and concentrated. The mixture was separated by column chromatography to obtain 16.2 g of the compound I1-6c. (Yield 45%)

(2) Compound 1-6

5. Synthesis of Compound 1-7

(1) compound I1-7c

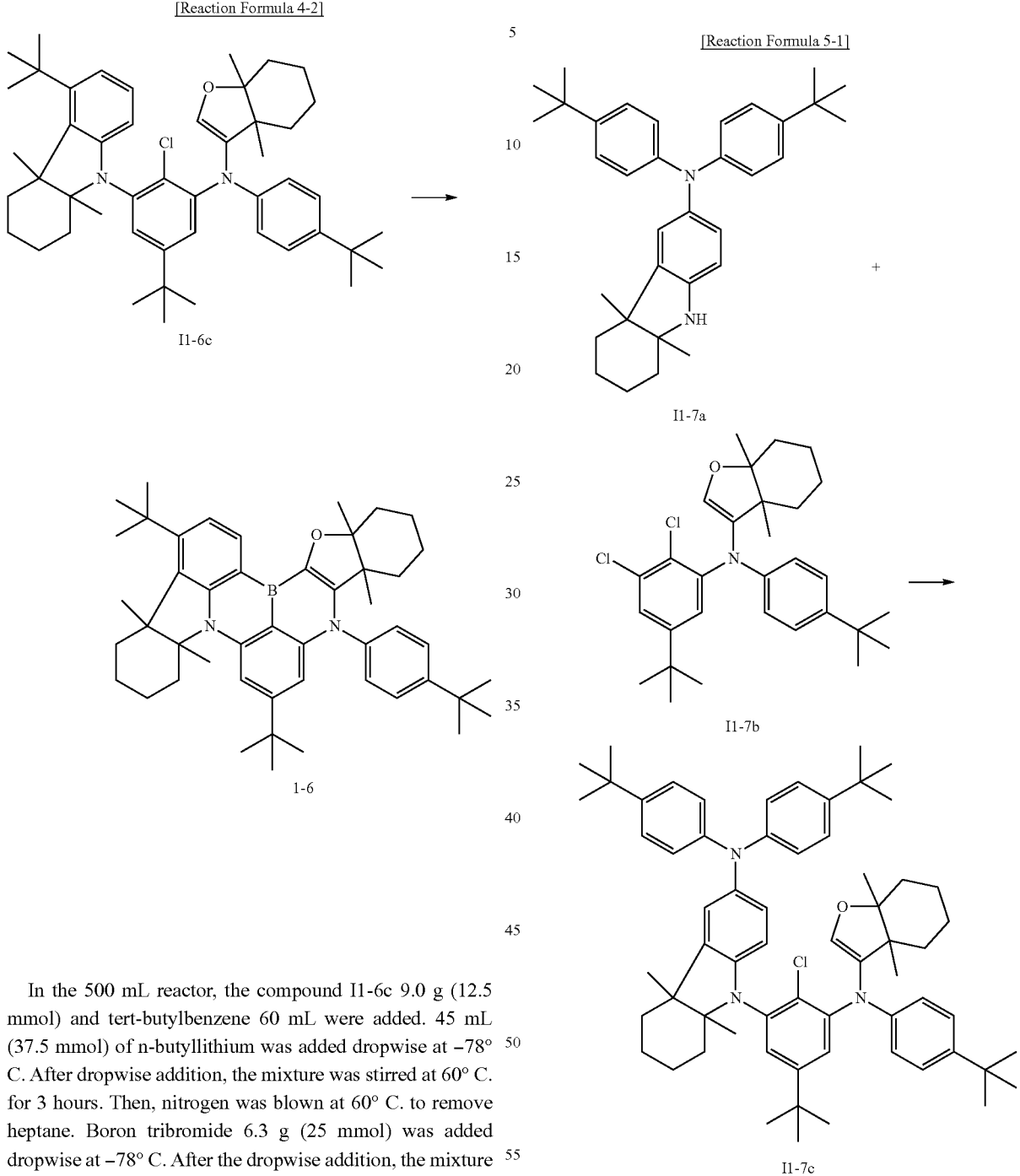

In the 500 mL reactor, the compound I1-6c 9.0 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.0 g of the compound 1-6. (Yield 11%)

In the 500 mL reactor, the compound I1-7a 24.0 g (50 mmol), the compound I1-7b 25.0 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred/refluxed for 5 hours. After completion of the reaction, the resultant was filtered and concentrated. The mixture was separated by column chromatography to obtain 22.7 g of the compound I1-7c. (Yield 48%)

(2) Compound 1-7

6. Synthesis of Compound 2-2

(1) Compound I2-2c

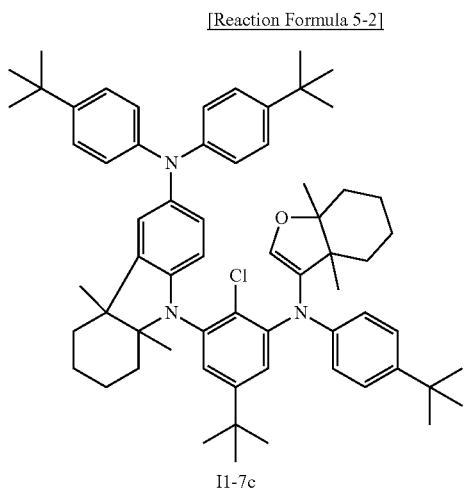

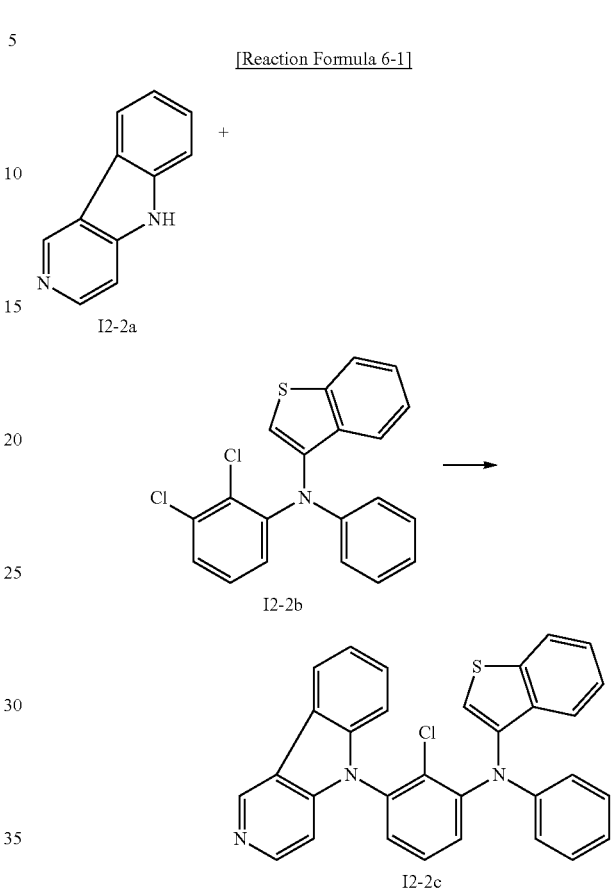

In the 500 mL reactor, the compound I2-2a 8.4 g (50 mmol), the compound I2-2b 18.5 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred under reflux for 5 hours. After the reaction was completed, the resultant was filtered and concentrated. The mixture was separated by column chromatography to obtain 12.8 g of the compound I2-2c. (Yield 51%)

(2) Compound 2-2

In the 500 mL reactor, the compound I1-7c 11.8 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.5 g of the compound 1-7. (Yield 13%)

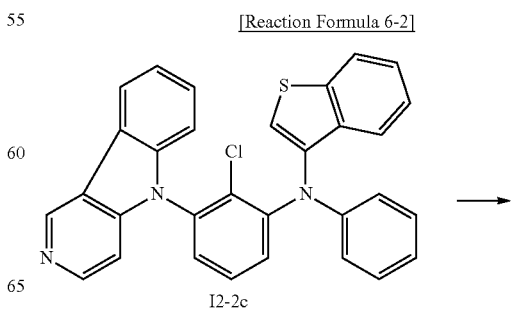

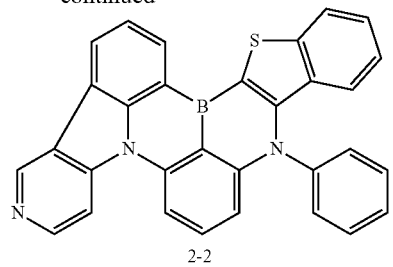

2-2

In the 500 mL reactor, the compound I2-2c 6.3 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 0.8 g of the compound 2-2. (Yield 14%)

7. Synthesis of Compound 2-3
(1) Compound I2-3c

[Reaction Formula 7-1]

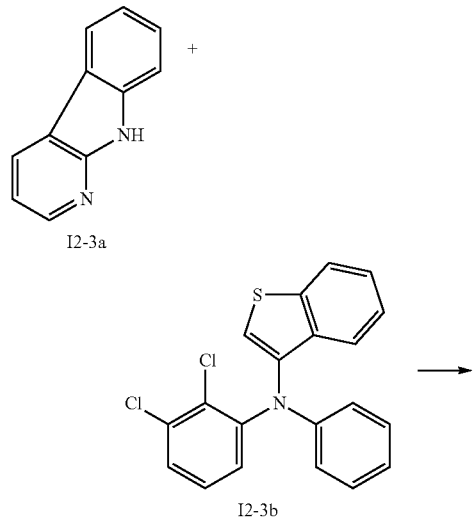

In the 500 mL reactor, the compound I2-3a 8.4 g (50 mmol), the compound I2-3b 18.5 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred under reflux for 5 hours. After completion of the reaction, the resultant was filtered and concentrated. The mixture was separated by column chromatography to obtain 14.6 g of the compound I2-3c. (Yield 58%)

(2) Compound 2-3

[Reaction Formula 7-2]

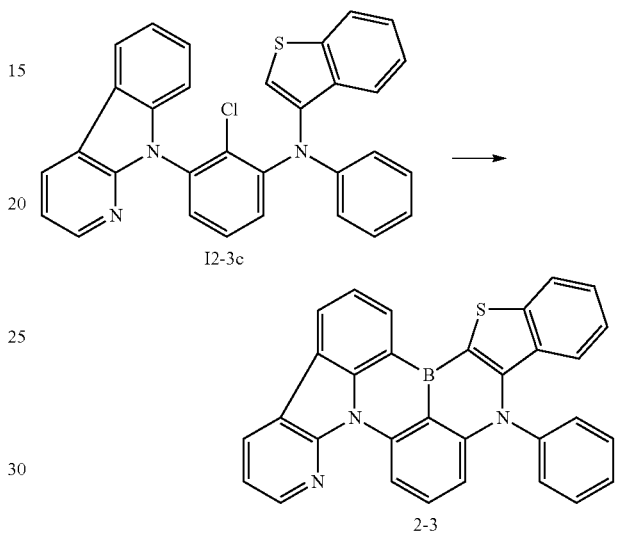

2-3

In the 500 mL reactor, the compound I2-3c 6.3 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.2 g of the compound 2-3. (Yield 20%)

8. Synthesis of Compound 2-5
(1) Compound I2-5c

[Reaction Formula 8-1]

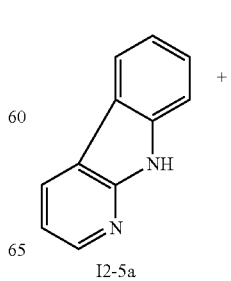

I2-5a

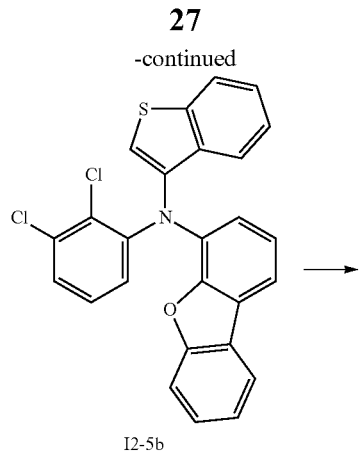

I2-5b

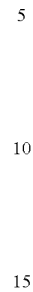

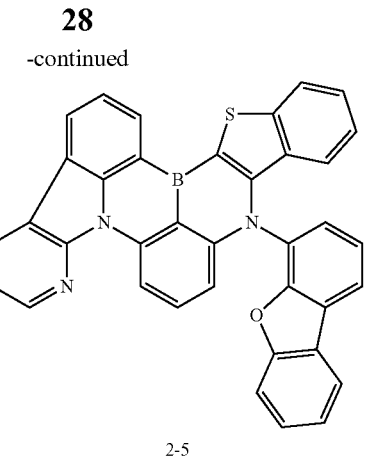

2-5

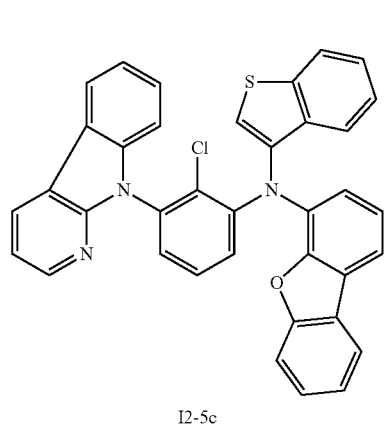

I2-5c

In the 500 mL reactor, the compound I2-5a 8.4 g (50 mmol), the compound I2-5b 23.0 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred under reflux for 5 hours. After the reaction was completed, the resultant was filtered and concentrated. The mixture was separated by column chromatography to obtain 16.2 g of the compound I2-5c. (Yield 55%)

(2) Compound 2-5

[Reaction Formula 8-2]

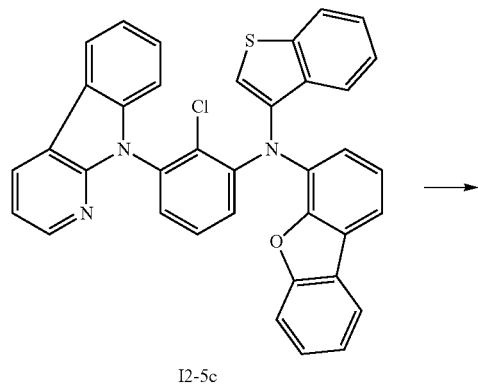

I2-5c

In the 500 mL reactor, the compound I2-5c 7.4 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.3 g of the compound 2-5. (Yield 18%)

9. Synthesis of Compound 2-7

(1) Compound I2-7c

[Reaction Formula 9-1]

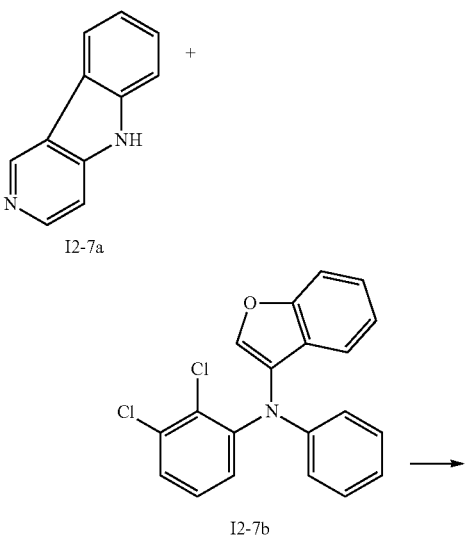

I2-7a

I2-7b

10. Synthesis of Compound 2-9

(1) Compound I2-9c

[Reaction Formula 10-1]

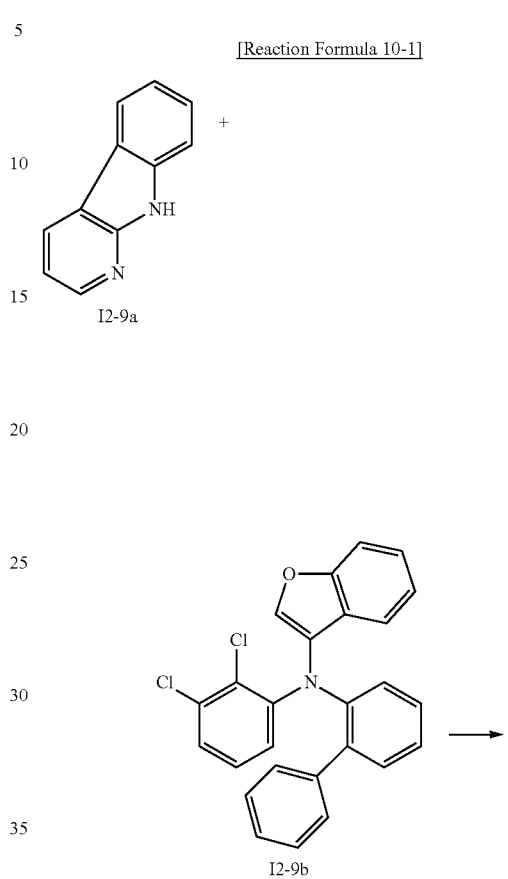

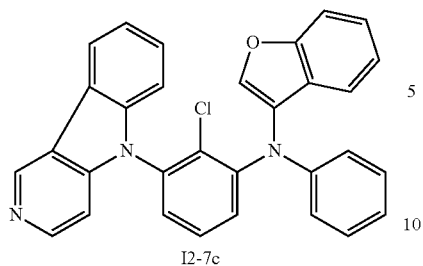

In the 500 mL reactor, the compound I2-7a 8.4 g (50 mmol), the compound I2-7b 17.7 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred under reflux for 5 hours. After the reaction was completed, the resultant was filtered and concentrated. The mixture was separated by column chromatography to obtain 14.8 g of the compound I2-7c. (Yield 61%)

(2) Compound 2-7

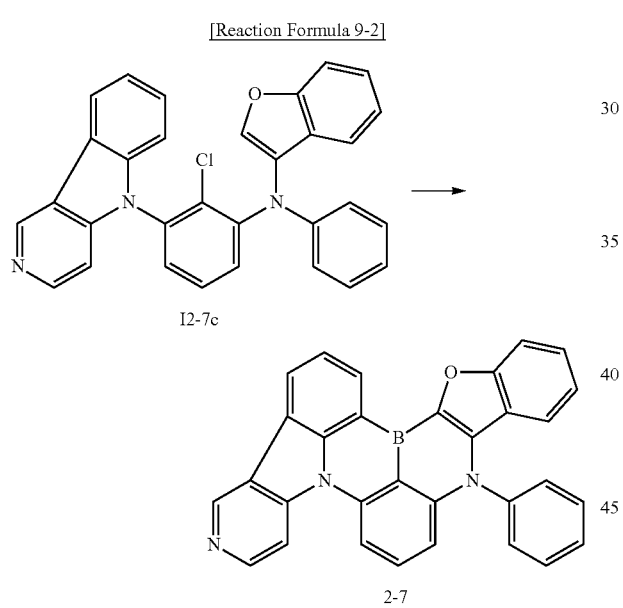

In the 500 mL reactor, the compound I2-7c 6.1 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.0 g of the compound 2-7. (Yield 17%)

In the 500 mL reactor, the compound I2-9a 8.4 g (50 mmol), the compound I2-9b 21.5 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred under reflux for 5 hours. After the reaction was completed, the resultant was filtered and concentrated. The mixture was separated by column chromatography to obtain 15.2 g of the compound I2-9c. (Yield 54%)

(2) Compound 2-9

[Reaction Formula 10-2]

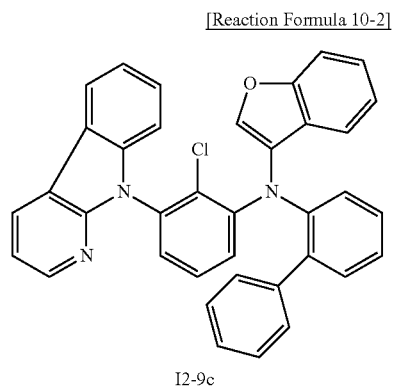

I2-9c

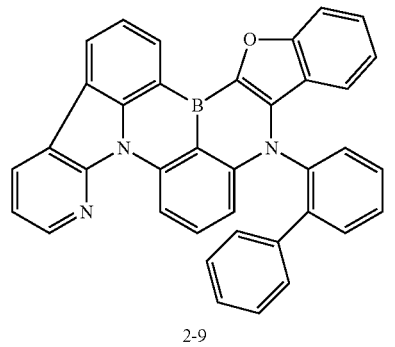

2-9

In the 500 mL reactor, the compound I2-9c 7.0 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.1 g of the compound 2-9. (Yield 16%)

11. Synthesis of Compound 2-10

(1) Compound I2-10c

[Reaction Formula 11-1]

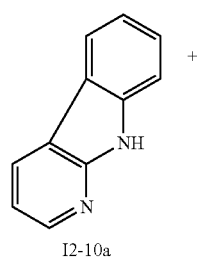

I2-10a

+

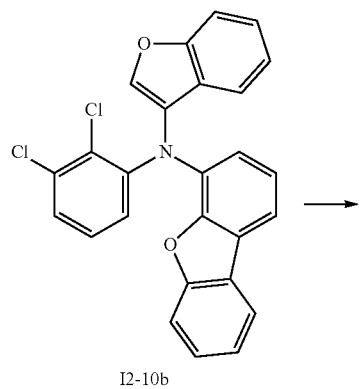

I2-10b

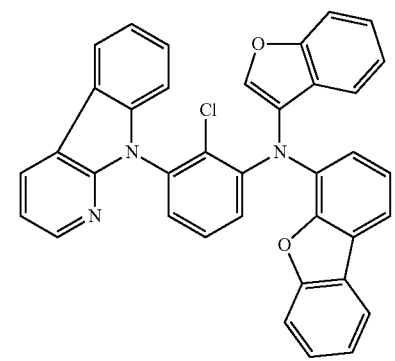

I2-10c

In the 500 mL reactor, the compound I2-10a 8.4 g (50 mmol), the compound I2-10b 22.2 g (50 mmol), palladium acetate 0.45 g (2 mmol), sodium tert-butoxide 18.9 g (196 mmol), tri-tert-butylphosphine 0.8 g (4 mmol) and 300 mL of toluene were added and stirred under reflux for 5 hours. After the reaction was completed, the resultant was filtered and concentrated. The mixture was separated by column chromatography to obtain 16.4 g of the compound I2-10c. (Yield 57%)

(2) Compound 2-10

[Reaction Formula 11-2]

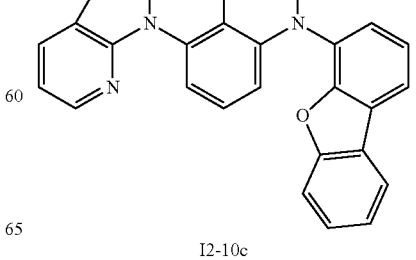

I2-10c

-continued

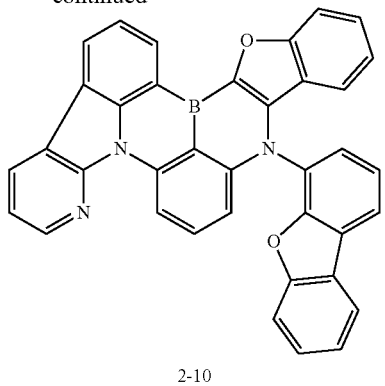

2-10

In the 500 mL reactor, the compound I2-10c 7.2 g (12.5 mmol) and tert-butylbenzene 60 mL were added. 45 mL (37.5 mmol) of n-butyllithium was added dropwise at −78° C. After dropwise addition, the mixture was stirred at 60° C. for 3 hours. Then, nitrogen was blown at 60° C. to remove heptane. Boron tribromide 6.3 g (25 mmol) was added dropwise at −78° C. After the dropwise addition, the mixture was stirred at room temperature for 1 hour, and 3.2 g (25 mmol) of N,N-diisopropylethylamine was added dropwise at 0° C. After dropwise addition, the mixture was stirred at 120° C. for 2 hours. After the reaction was completed, an aqueous sodium acetate solution was added thereto and stirred at room temperature. The mixture was extracted with ethyl acetate, the organic layer was concentrated, and separated by column chromatography to obtain 1.2 g of the compound 2-10. (Yield 18%)

In the EML 240, the first compound 242 acts as a dopant (emitter) to emit the blue light.

In addition, the EML 240 can further include a second compound 244 as a host. In this instance, in the EML 240, the first compound 242 can have a weight % of about 0.1 weight % to 30 weight %, preferably about 0.1 weight % to 10 weight %, and more preferably about 1 weight % to 5 weight %. The EML 240 can have a thickness of about 10 to 500 Å, preferably about 50 to 400 Å, and more preferably about 100 to 300 Å.

The second compound 244 as the host can be an anthracene derivative. For example, the second compound 244 can be represented by Formula 4.

[Formula 4]

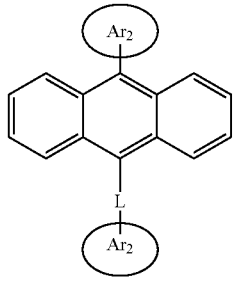

In Formula 4, each of $Ar_1$ and $Ar_2$ is independently unsubstituted or substituted C6 to C30 aryl group or unsubstituted or substituted C5 to C30 heteroaryl group. L is a single bond or C6 to C30 arylene group. In this instance, hydrogens in the anthracene derivative are not deuterated or partially or wholly deuterated. Namely, none, a part or all of the hydrogens in the anthracene derivative is substituted by deuterium.

In Formula 4, each of $Ar_1$ and $Ar_2$ can be selected from the group consisting of phenyl, naphthyl, dibenzofuranyl and fused dibenzofuranyl, and L can be the single bond or phenylene.

For example, $Ar_1$ can be selected from the group consisting of naphthyl, dibenzofuranyl, phenyl-dibenzofuranyl and fused dibenzofuranyl, and $Ar_2$ can be selected from the group consisting of phenyl and naphthyl. In an embodiment, $Ar_1$ and $Ar_2$ can be naphthyl, and L can be the single bond or phenylene.

In Formula 4, the anthracene core can be partially or wholly deuterated, or each of $Ar_1$, $Ar_2$, L can be partially or wholly deuterated. Alternatively, each of the anthracene core, $Ar_1$, $Ar_2$, L can be partially or wholly deuterated.

The second compound 244 in Formula 4 can be one of compounds in Formula 5.

[Formula 5]

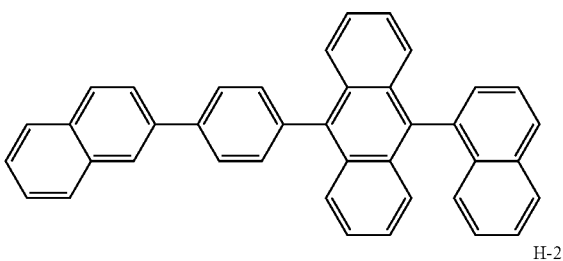

H-1

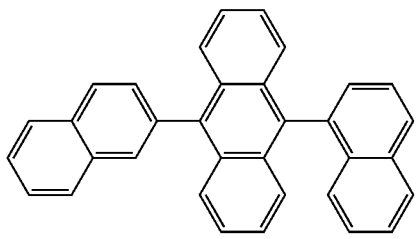

H-2

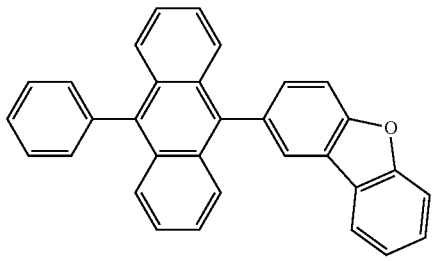

H-3

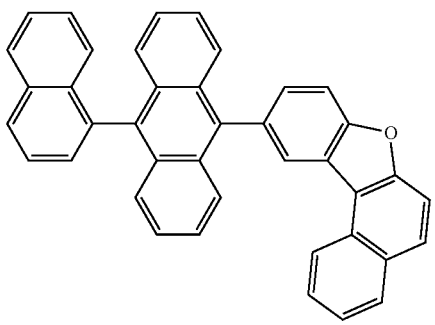

H-4

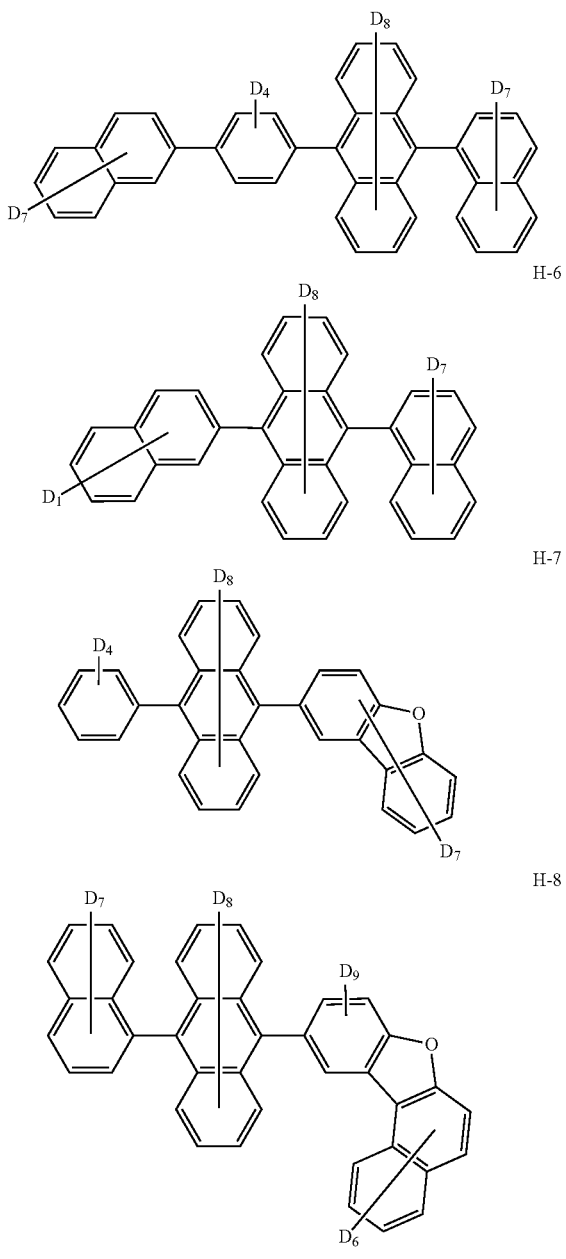

(dipyrazino[2,3-f:2'3'-h]quinoxaline-2,3,6,7,10,11-hexacarbonitrile (HAT-CN), 1,3,5-tris[4-(diphenylamino)phenyl] benzene (TDAPB), poly(3,4-ethylenedioxythiophene) polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine. Alternatively, the HIL 210 can include a compound in Formula 12 below as a host and a compound in Formula 13 below as a dopant.

The HTL 220 can include at least one compound selected from the group consisting of N,N'-diphenyl-N,N'-bis(3-methylphenyl)-1,1'-biphenyl-4,4'-diamine (TPD), NPB (or NPD), 4,4'-bis(N-carbazolyl)-1,1'-biphenyl (CBP), poly[N,N'-bis(4-butylphenyl)-N,N'-bis(phenyl)-benzidine] (poly-TPD), (poly[(9,9-dioctylfluorenyl-2,7-diyl)-co-(4,4'-(N-(4-sec-butylphenyl)diphenylamine))] (TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl-4-amine. Alternatively, the HTL 220 can include a compound of Formula 12 below.

The EBL 230, which is disposed between the HTL 220 and the EML 240, is formed to prevent the electron toward the HTL 220. The EBL 230 includes the electron blocking material of the amine derivative. The electron blocking material is represented by Formula 6.

[Formula 6]

In Formula 6, L is C6 to C30 arylene group, and a is 0 or 1. Each of $R_1$ and $R_2$ is independently selected from the group consisting of unsubstituted or substituted C6 to C30 aryl group and unsubstituted or substituted C5 to C30 heteroaryl group.

For example, L can be phenylene, and each of $R_1$ and $R_2$ can be selected from the group consisting of biphenyl, dimethyl substituted fluorenyl, carbazolyl, phenylcarbazolyl, carbazolylphenyl, dibenzothiophenyl and dibenzofuranyl.

Namely, the electron blocking material can be an amine derivative substituted by spirofluorene (e.g., "spirofluorene-substituted amine derivative").

The electron blocking material of Formula 6 can be one of the followings of Formula 7:

The HIL 210 can include at least one compound selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino) triphenylamine (2T-NATA), copper phthalocyanine(CuPc), tris(4-carbazoyl-9-yl-phenyl)amine (TCTA), N,N'-diphenyl-N,N'-bis(1-naphthyl)-1,1'-biphenyl-4,4"-diamine (NPB or NPD), 1,4,5,8,9,11-hexaazatriphenylenehexacarbonitrile

[Formula 7]
EBL-1
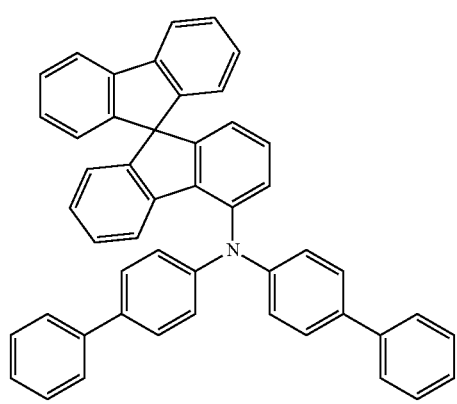
EBL-2
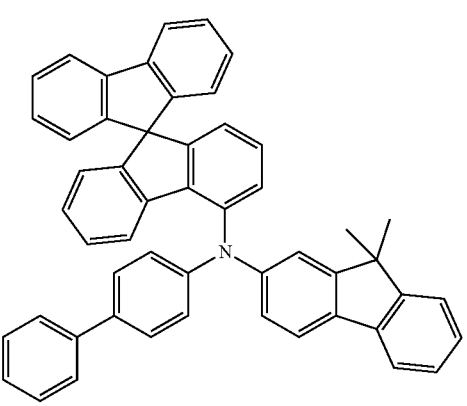
EBL-3
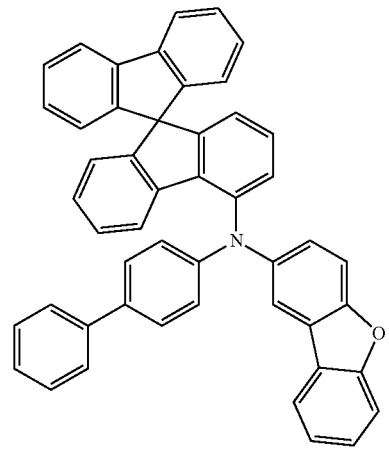
-continued
EBL-4
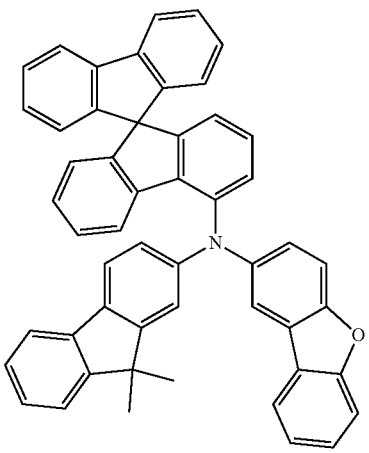
EBL-5
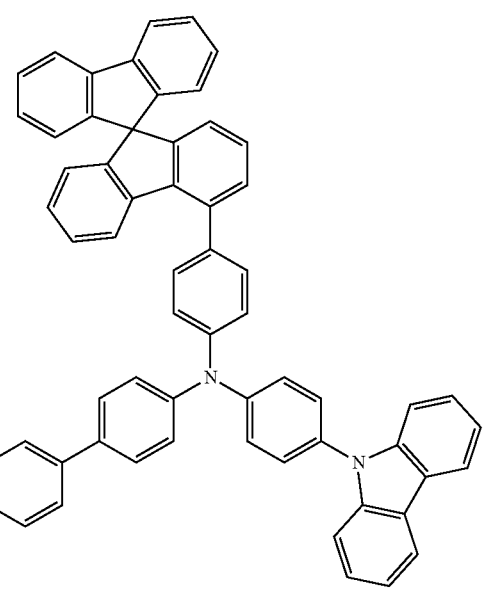
EBL-6
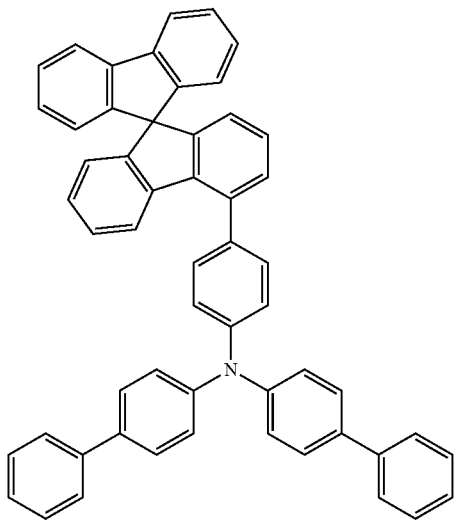

EBL-7

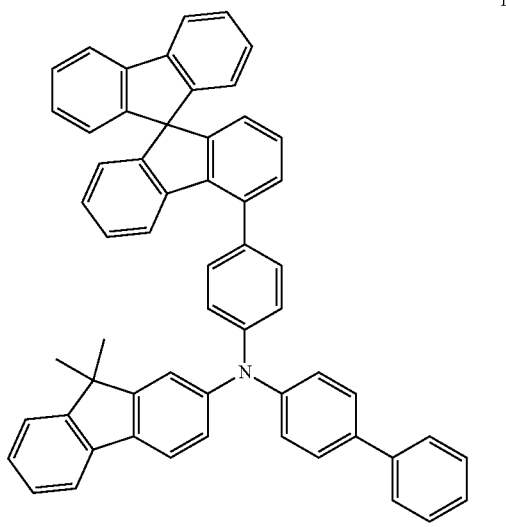

EBL-8

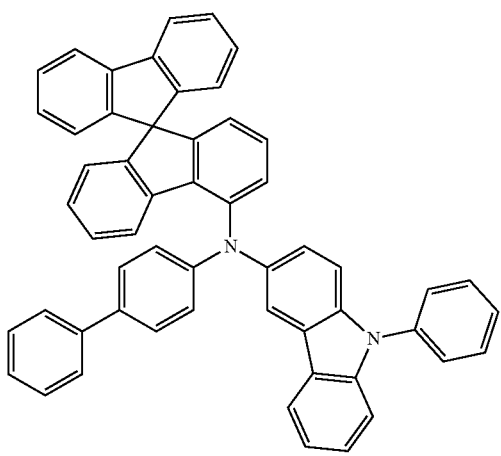

EBL-9

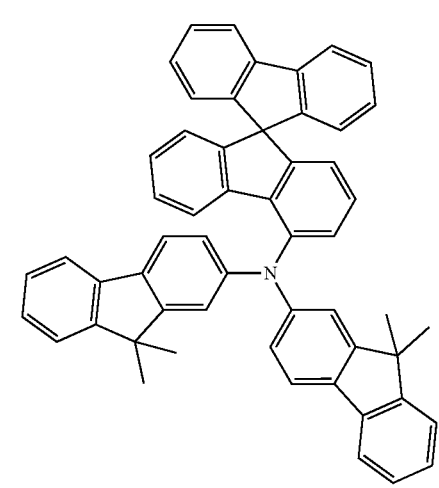

EBL-10

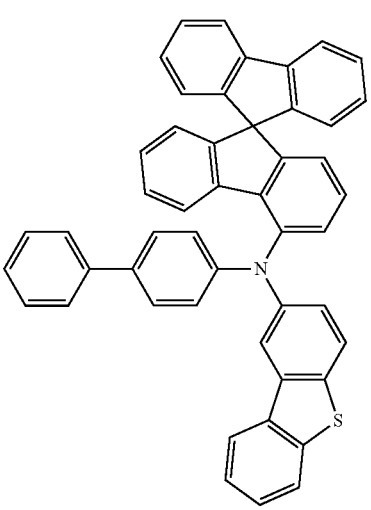

EBL-11

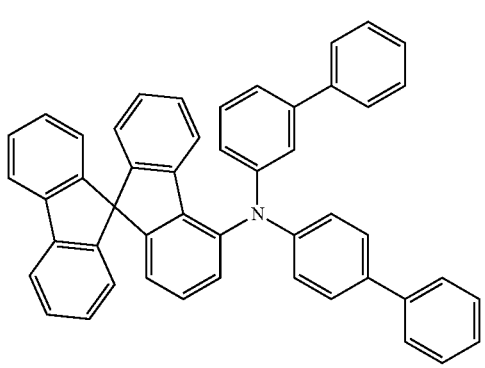

The HBL 250, which is disposed between the EML 240 and the EIL 260, is formed to prevent the hole toward the EIL 260. The HBL 250 includes the hole blocking material of the azine derivative. The azine derivative as the hole blocking material is represented by Formula 8.

[Formula 8]

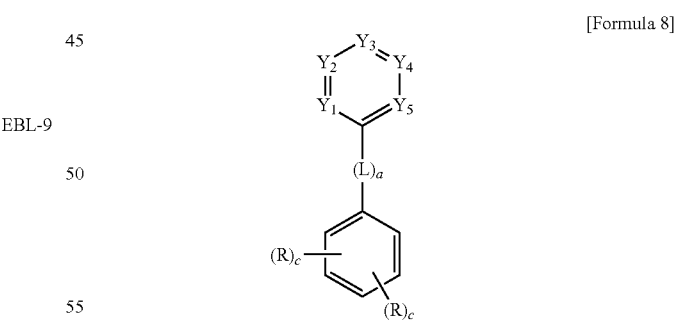

In Formula 8, each of $Y_1$ to $Y_5$ is independently $CR_1$ or N, and one to three of $Y_1$ to $Y_5$ is N. $R_1$ is independently C6~C30 aryl group. L is $C_6$~$C_{30}$ arylene group, and $R_2$ is C6~C30 aryl group or C5-C30 hetero aryl group, wherein the C6~C30 aryl group is optionally substituted with another C6~C30 aryl group or C5~C30 hetero aryl group or forms a spiro structure with a C10~C30 fused aryl ring or a C10~C30 fused hetero aryl ring, wherein the another C6~C30 aryl is optionally further substituted with other C6~C30 or C5~C30 hetero aryl or forms a spiro structure with a C10~C30 fused aryl ring. R₃ is hydrogen, or adjacent two of R₃ form a fused ring. "a" is 0 or 1, "b" is 1 or 2, and "c" is an integer of 0 to 4.
The hole blocking material of Formula 8 can be one of the followings of Formula 9.
[Formula 9]
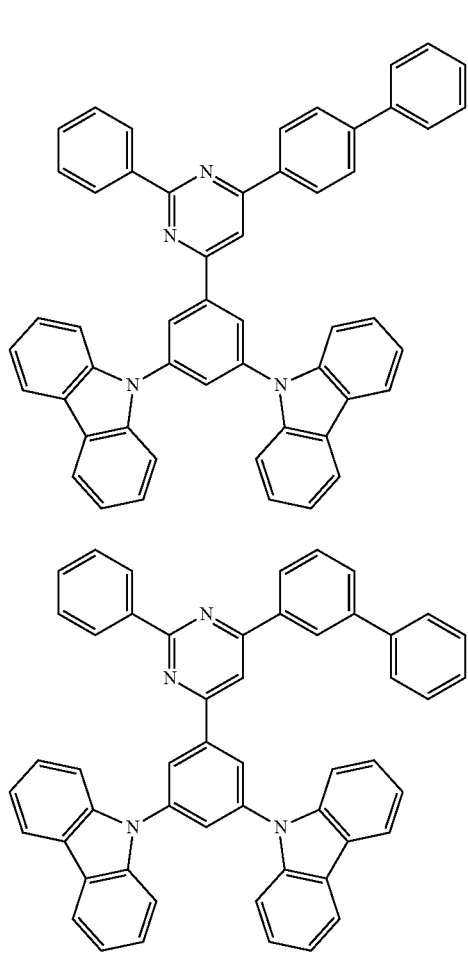
E1
E2
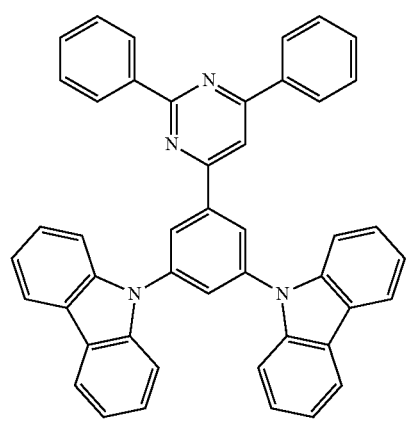
E3
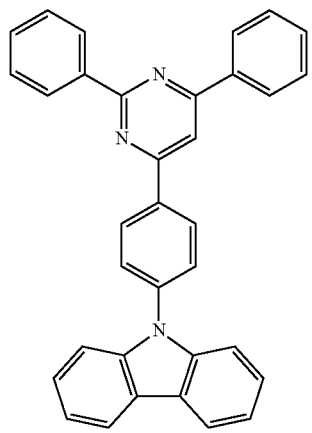
E4
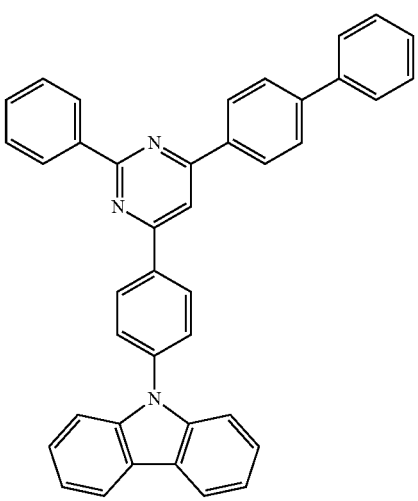
E5
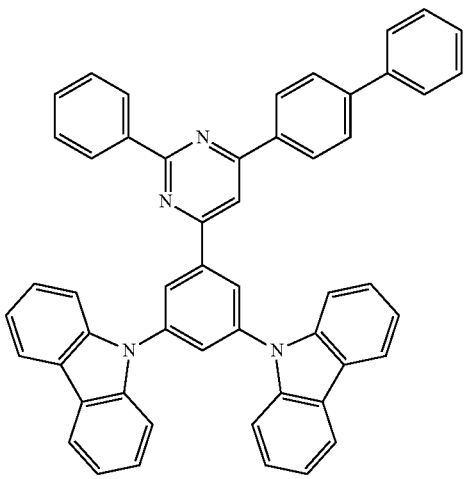
E6

E7
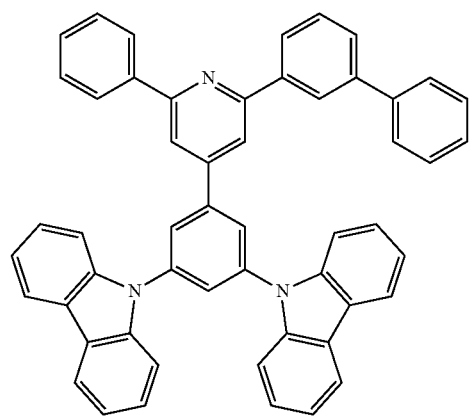
E8
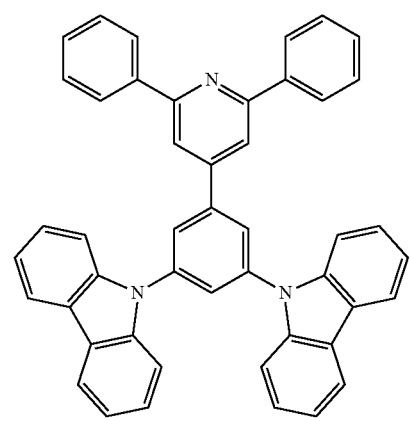
E9
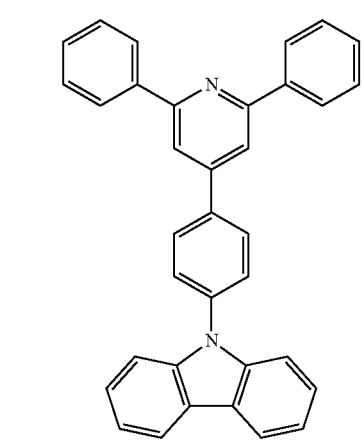
E10
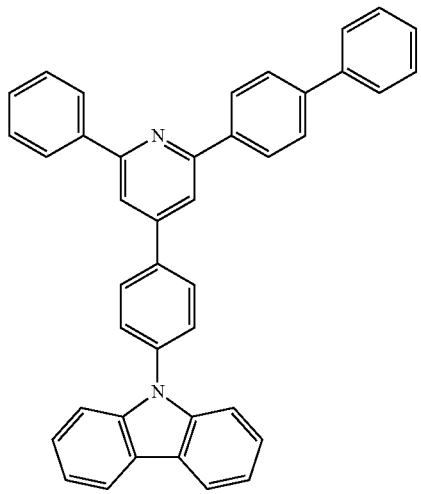
E11
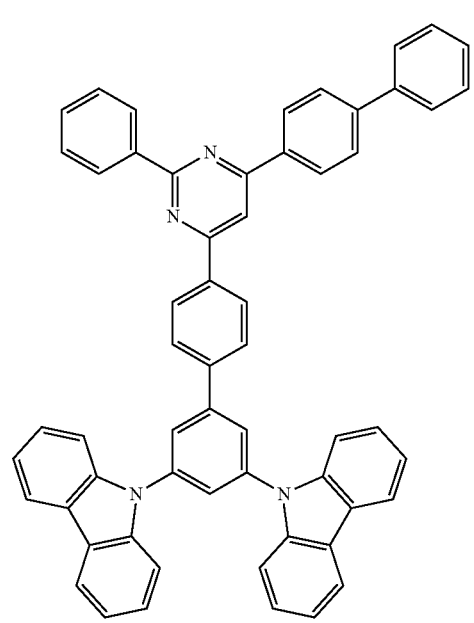
E12
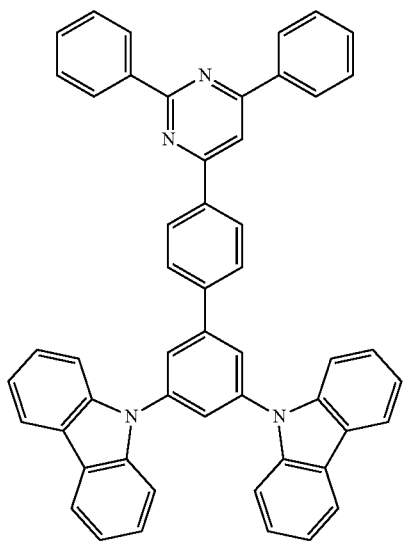

E13
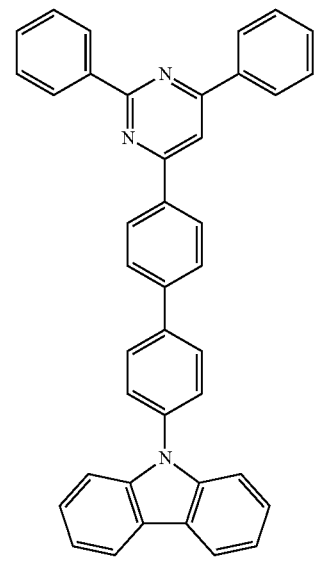
E14
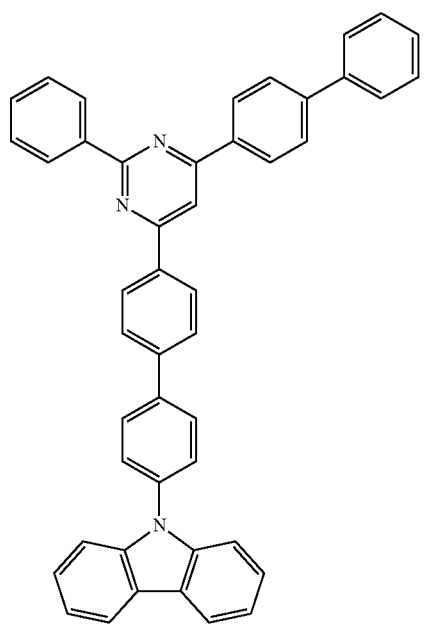
E15
E16
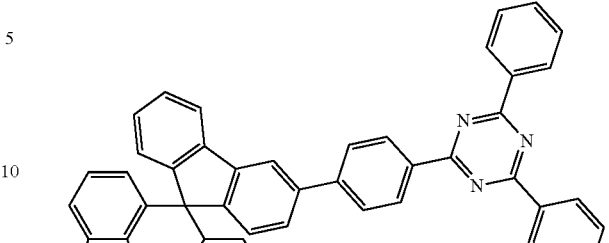
E17
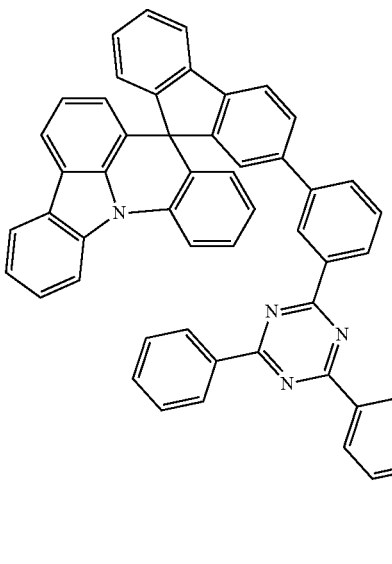
E18
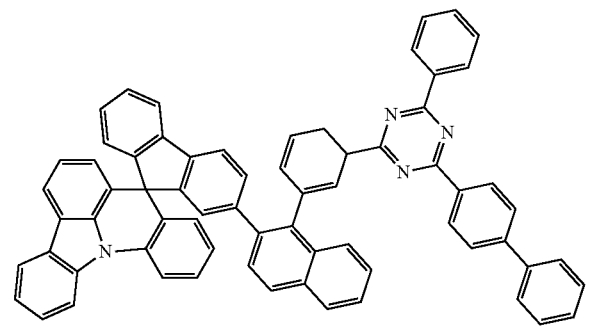

E19
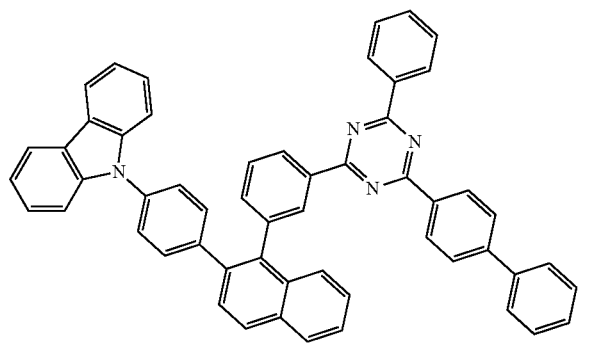

E20
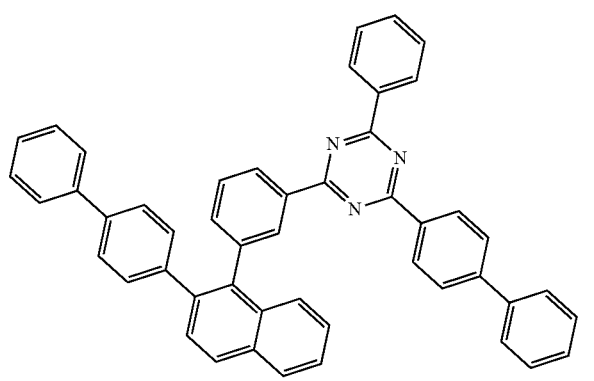

E21
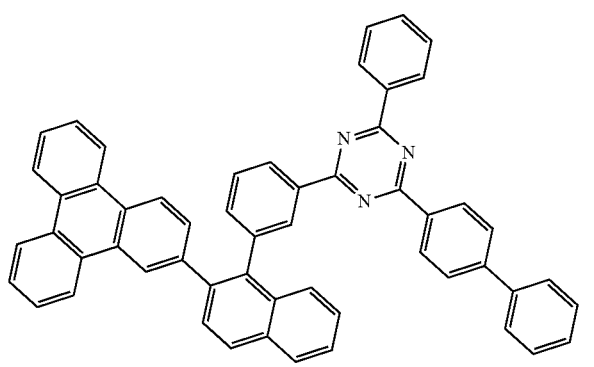

E22
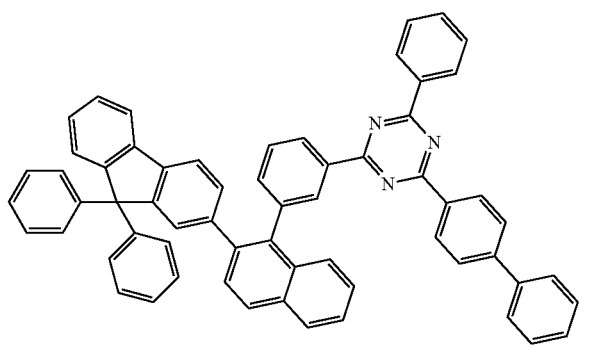

E23
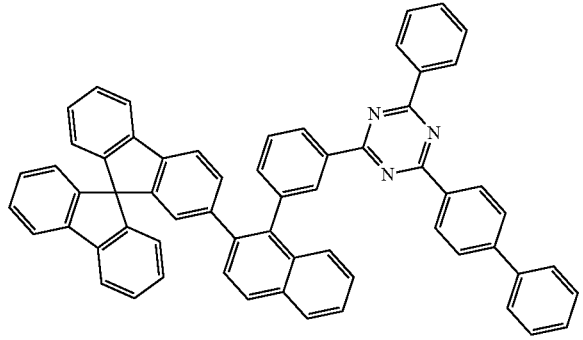

Alternatively, the HBL 250 can include the benzimidazole derivative as the hole blocking material. For example, the benzimidazole derivative as the hole blocking material is represented by Formula 10.

[Formula 10]

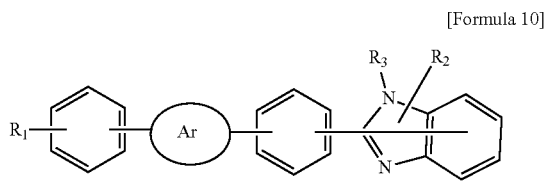

In Formula 10, Ar is $C_{10}$~$C_{30}$ arylene group, $R_1$ is $C_6$~$C_{30}$ aryl group or $C_5$~$C_{30}$ hetero aryl group, each of the $C_6$~$C_{30}$ aryl group and the $C_5$~$C_{30}$ hetero aryl group is optionally substituted with $C_1$-$C_{10}$ alkyl, and each of $R_2$ and $R_3$ is independently hydrogen, $C_1$~$C_{10}$ alkyl group or $C_6$~$C_{30}$ aryl group.

For example, Ar can be naphthylene or anthracenylene, $R_1$ can be benzimidazole or phenyl, $R_2$ can be methyl, ethyl or phenyl, and $R_3$ can be hydrogen, a methyl group or a phenyl group.

The hole blocking material of Formula 10 can be one of the followings of Formula 11.

[Formula 11]

F1
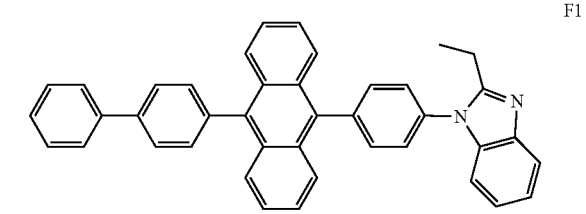

F2
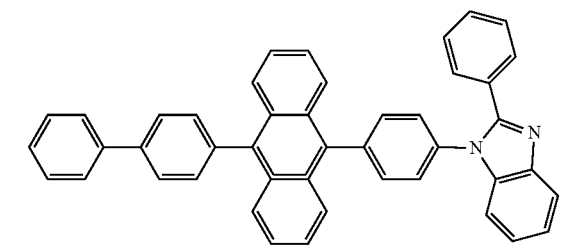

F3

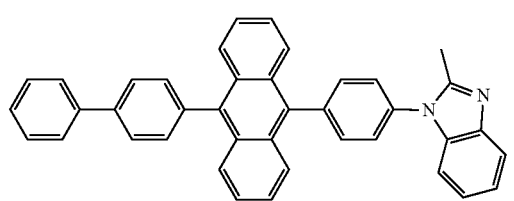

F4

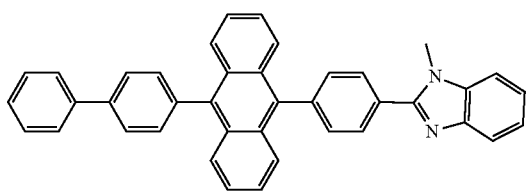

F5

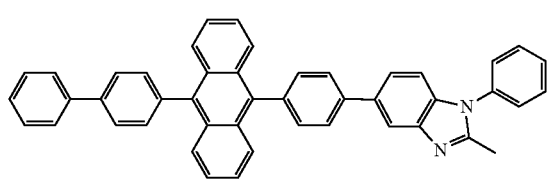

F6

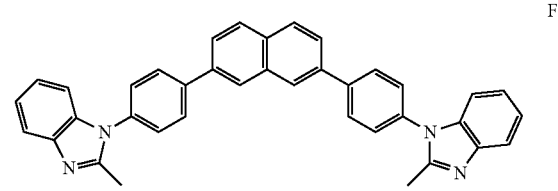

The HBL 250 can include at least one of the hole blocking material in Formula 8 and the hole blocking material in Formula 10.

In this instance, a thickness of EML 240 can be greater than each of that of the EBL 230 and the HBL 250 and can be smaller than that of the HTL 220. For example, the EML 240 can have a thickness of about 150 to 250 Å, each of the EBL 230 and the HBL 250 can have a thickness of about 50 to 150 Å, and the HTL 220 can have a thickness of about 900 to 1100 Å. The EBL 230 and the HBL 250 can have the same thickness.

The HBL 250 can include the compound in Formula 8 and the compound in Formula 10. For example, in the HBL 250, the compound in Formula 8 and the compound in Formula 10 can have the same weight %.

In this instance, a thickness of the EML 240 can be greater than that of the EBL 230 and can be smaller than that of the HBL 250. In addition, the thickness of the HBL 250 can be smaller than that of the HTL 220. For example, the EML 240 can have a thickness of about 200 to 300 Å, and the EBL can have a thickness of about 50 to 150 Å. The HBL 250 can have a thickness of about 250 to 350 Å, and the HTL 220 can have a thickness of about 800 to 1000 Å.

The hole blocking material in Formula 8 and/or Formula 10 has excellent hole blocking property and excellent electron transporting property. Accordingly, an electron transporting layer can be presented, and the HBL 250 can directly contact the EIL 260 or the second electrode 164.

The EIL 260 can include at least one of an alkali metal, such as Li, an alkali halide compound, such as LiF, CsF, NaF, or BaF$_2$, and an organo-metallic compound, such as Liq, lithium benzoate, or sodium stearate, but it is not limited thereto. Alternatively, the EIL 260 can include a compound of Formula 14 below as a host and an alkali metal as a dopant.

In the OLED D, the EML 240 includes the emitting compound 242 in Formula 1 such that the lifespan of the OLED D and the organic light emitting display device 100 is significantly improved.

[Organic Light Emitting Diode]

The anode (ITO, 0.5 mm), the HIL (Formula 12 (97 wt %) and Formula 13 (3 wt %), 100 Å), the HTL (Formula 12, 1000 Å), the EBL (the compound EBL-11 in Formula 7, 100 Å), the EML (the compound H-1 in Formula 5 (host, 98 wt %) and dopant (2 wt %), 200 Å), the HBL (the compound E1 in Formula 9, 100 Å), the EIL (Formula 14 (98 wt %) and Li (2 wt %), 200 Å) and the cathode (Al, 500 Å) was sequentially deposited. An encapsulation film is formed by using an UV curable epoxy and a moisture getter to form the OLED.

[Formula 12]

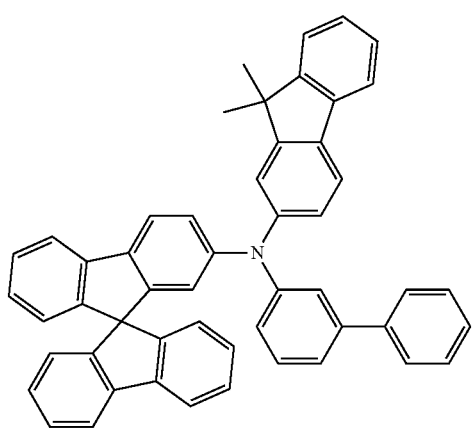

[Formula 13]

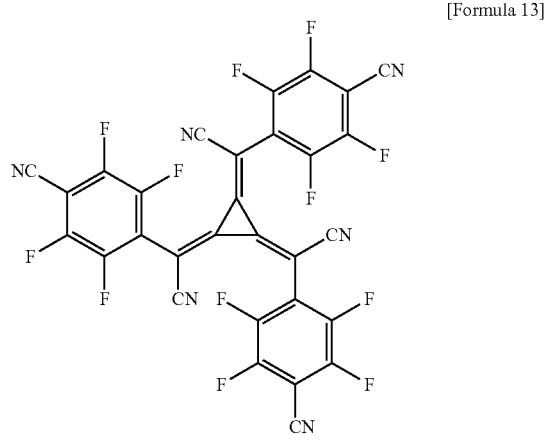

-continued

[Formula 14]

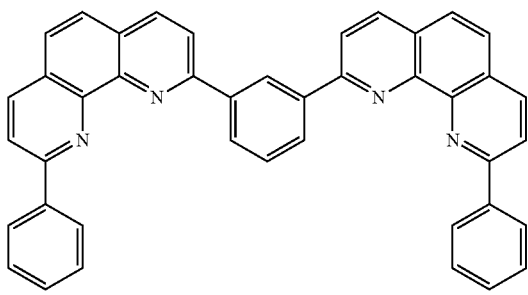

(1) Comparative Examples 1 and 2 (Ref1 and Ref2)

The compound "Ref-1" in Formula 15 and the compound "Ref-2" in Formula 16 are respectively used as the dopant to form the EML.

(2) Examples 1 to 11 (Ex1 to Ex11)

The compounds 1-1, 1-3, 1-4, 1-6, 1-7, 2-2, 2-3, 2-5, 2-7, 2-9 and 2-10 in Formula 3 are respectively used as the dopant to form the EML.

[Formula 15]

Ref-1

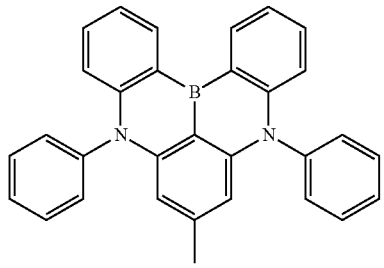

[Formula 16]

Ref-2

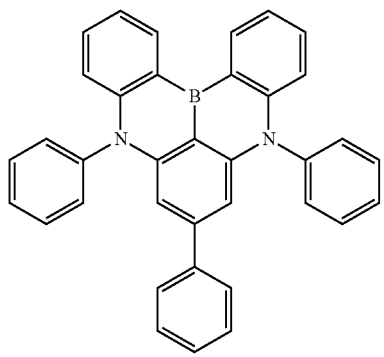

The properties, i.e., voltage (V), external quantum efficiency (EQE), color coordinate (CIE) and lifespan ($T_{95}$), of the OLEDs manufactured in Comparative Examples 1 and 2 and Examples 1 to 11 are measured and listed in Table 1. The properties of the OLED were measured at the room temperature using a current source (KEITHLEY) and a photometer (PR 650). The driving voltage, the external quantum efficiency, and the color coordinate were measured under the condition of a current density of 10 mA/cm², and the lifespan $T_{95}$ (the time to reach 95% of the lifespan) was measured at 40° C. under the 22.5 mA/cm² condition.

TABLE 1

| | Dopant | V | EQE (%) | CIE(x, y) | $T_{95}$ (hr) |
|---|---|---|---|---|---|
| Ref1 | Ref-1 | 3.95 | 6.31 | (0.140, 0.060) | 76 |
| Ref2 | Ref-2 | 3.94 | 6.28 | (0.140, 0.075) | 72 |
| Ex1 | 1-1 | 3.93 | 6.29 | (0.140, 0.085) | 113 |
| Ex2 | 1-3 | 3.92 | 6.14 | (0.141, 0.087) | 121 |
| Ex3 | 1-4 | 3.90 | 6.45 | (0.140, 0.086) | 98 |
| Ex4 | 1-6 | 3.91 | 5.92 | (0.142, 0.084) | 102 |
| Ex5 | 1-7 | 3.89 | 6.17 | (0.140, 0.083) | 107 |
| Ex6 | 2-2 | 3.96 | 6.63 | (0.140, 0.132) | 120 |
| Ex7 | 2-3 | 3.95 | 6.65 | (0.141, 0.129) | 108 |
| Ex8 | 2-5 | 3.99 | 6.48 | (0.140, 0.133) | 116 |
| Ex9 | 2-7 | 3.96 | 6.52 | (0.141, 0.132) | 103 |
| Ex10 | 2-9 | 3.94 | 6.41 | (0.141, 0130) | 125 |
| Ex11 | 2-10 | 3.95 | 6.47 | (0.140, 0.129) | 101 |

As shown in Table 1, in comparison to the OLED of Ref1 and Ref2, the lifespan of the OLED in Ex1 to Ex11 using the emitting compound of the present disclosure as the dopant is significantly improved.

Figure 4:
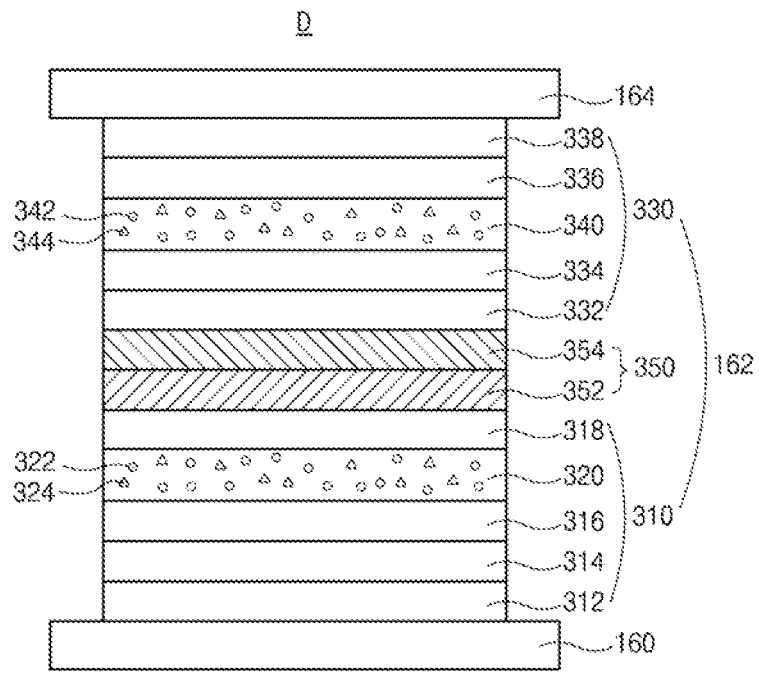
FIG. 4 is a schematic cross-sectional view illustrating an OLED having a tandem structure of two emitting parts for the organic light emitting display device according to the first embodiment of the present disclosure.

FIG. 4 is a schematic cross-sectional view illustrating an OLED having a tandem structure of two emitting units for the organic light emitting display device according to the first embodiment of the present disclosure.

As shown in FIG. 4, the OLED D includes the first and second electrodes 160 and 164 facing each other and the organic emitting layer 162 between the first and second electrodes 160 and 164. The organic emitting layer 162 includes a first emitting part 310 including a first EML 320, a second emitting part 330 including a second EML 340 and a charge generation layer (CGL) 350 between the first and second emitting parts 310 and 330. The organic light emitting display device 100 (of FIG. 2) includes a red pixel, a green pixel and a blue pixel, and the OLED D is positioned in the blue pixel.

One of the first and second electrodes 160 and 164 is an anode, and the other one of the first and second electrodes 160 and 164 is cathode. In addition, one of the first and second electrodes 160 and 164 can be a transparent (or a semi-transparent) electrode, and the other one of the first and second electrodes 160 and 164 can be a reflection electrode.

The CGL 350 is positioned between the first and second emitting parts 310 and 330, and the first emitting part 310, the CGL 350 and the second emitting part 330 are sequentially stacked on the first electrode 160. Namely, the first emitting part 310 is positioned between the first electrode 160 and the CGL 350, and the second emitting part 330 is positioned between the second electrode 164 and the CGL 350.

The first emitting part 310 includes a first EML 320. In addition, the first emitting part 310 can further include a first EBL 316 between the first electrode 160 and the first EML 320 and a first HBL 318 between the first EML 320 and the CGL 350.

In addition, the first emitting part 310 can further include a first HTL 314 between the first electrode 160 and the first EBL 316 and an HIL 312 between the first electrode 160 and the first HTL 314.

The first EML 320 includes the emitting compound in Formula 1 as a first compound 322 and provides blue emission. For example, the first compound 322 in the first EML 320 can be one of the compounds in Formula 3.

The EML 320 can further include a second compound 324. For example, the second compound 324 can be represented by Formula 4 and can be one of the compounds in Formula 5.

In the first EML 320, the first compound 322 has a weight % being smaller than the second compound 324. The first compound 322 can act as a dopant (an emitter), and the second compound 324 can act as a host. For example, in the first EML 320, the first compound 322 can have a weight % of about 0.1 weight % to 30 weight %. To provide sufficient emitting efficiency and lifespan, the weight % of the first compound 322 can be about 0.1 weight % to 10 weight %, preferably about 1 weight % to 5 weight %.

The first EBL 316 can include the compound in Formula 6 as the electron blocking material. In addition, the first HBL 318 can include at least one of the compounds in Formula 8 and Formula 10 as the hole blocking material.

The second emitting part 330 includes the second EML 340. In addition, the second emitting part 330 can further include a second EBL 334 between the CGL 350 and the second EML 340 and a second HBL 336 between the second EML 340 and the second electrode 164.

In addition, the second emitting part 330 can further include a second HTL 332 between the CGL 350 and the second EBL 334 and an EIL 338 between the second HBL 336 and the second electrode 164.

The second EML 340 includes the emitting compound in Formula 1 as a third compound 342 and provides blue emission. For example, the third compound 342 in the second EML 340 can be one of the compounds in Formula 3.

The second EML 340 can further include a fourth compound 344. For example, the fourth compound 344 can be represented by Formula 4 and can be one of the compounds in Formula 5.

In the second EML 340, the third compound 342 can have a weight % being less than the fourth compound 344. In the second EML 340, the third compound 342 can act as a dopant (an emitter), and the fourth compound 344 can act as a host. For example, in the second EML 340, the third compound 342 has a weight % of about 0.1 weight % to 30 weight %. To provide sufficient emitting efficiency and lifespan, the weight % of the third compound 342 can be about 0.1 weight % to 10 weight %, preferably about 1 weight % to 5 weight %.

The third compound 342 in the second EML 340 and the first compound 322 in the first EML 320 can be same or different, and the fourth compound 344 in the second EML 340 and the second compound 324 in the first EML 320 can be same or different. In addition, the weight % of the first compound 322 in the first EML 320 and the weight % of the third compound 342 in the second EML 340 can be same or different.

The second EBL 334 can include the electron blocking material in Formula 6. In addition, the second HBL 336 can include at least one of the hole blocking material in Formula 8 and the hole blocking material in Formula 10.

The CGL 350 is positioned between the first and second emitting parts 310 and 330. Namely, the first and second emitting parts 310 and 330 are connected through the CGL 350. The CGL 350 can be a P-N junction CGL of an N-type CGL 352 and a P-type CGL 354.

The N-type CGL 352 is positioned between the first HBL 318 and the second HTL 332, and the P-type CGL 354 is positioned between the N-type CGL 352 and the second HTL 332.

In the OLED D, since each of the first and second EMLs 320 and 340 includes the emitting compound in Formula 1 as the first and third compounds 322 and 342, respectively, the emitting efficiency and the lifespan of the OLED D and the organic light emitting display device 100 are improved.

In addition, since the first and second emitting parts 310 and 330 for emitting blue light are stacked, the organic light emitting display device 100 provides an image having high color temperature.

Figure 5:
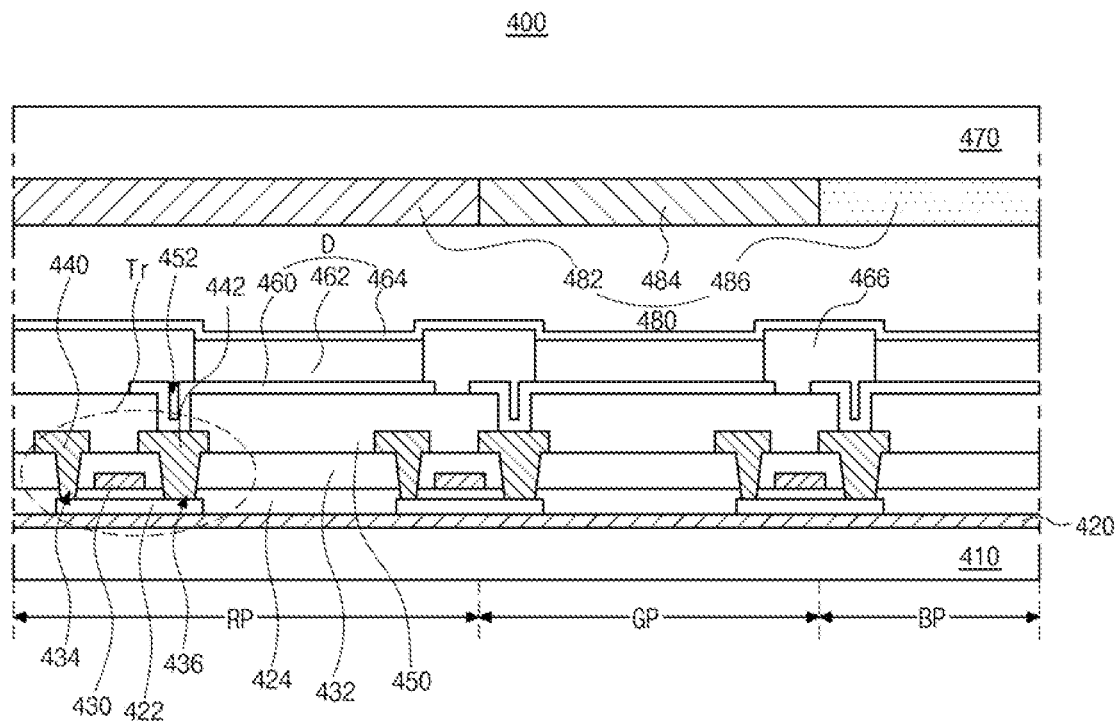
FIG. 5 is a schematic cross-sectional view illustrating an organic light emitting display device according to a second embodiment of the present disclosure.
Figure 6:
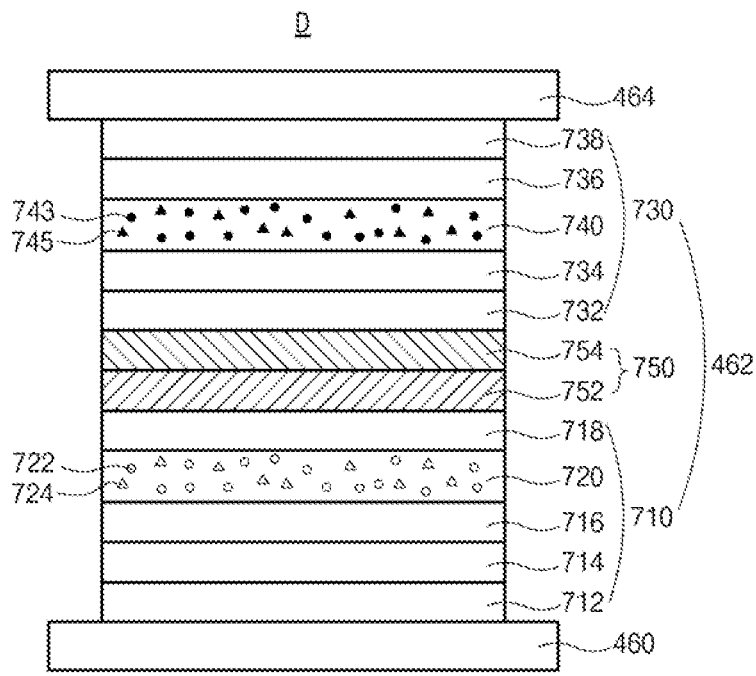
FIG. 6 is a schematic cross-sectional view illustrating an OLED having a tandem structure of two emitting parts for the organic light emitting display device according to the second embodiment of the present disclosure.
Figure 7:
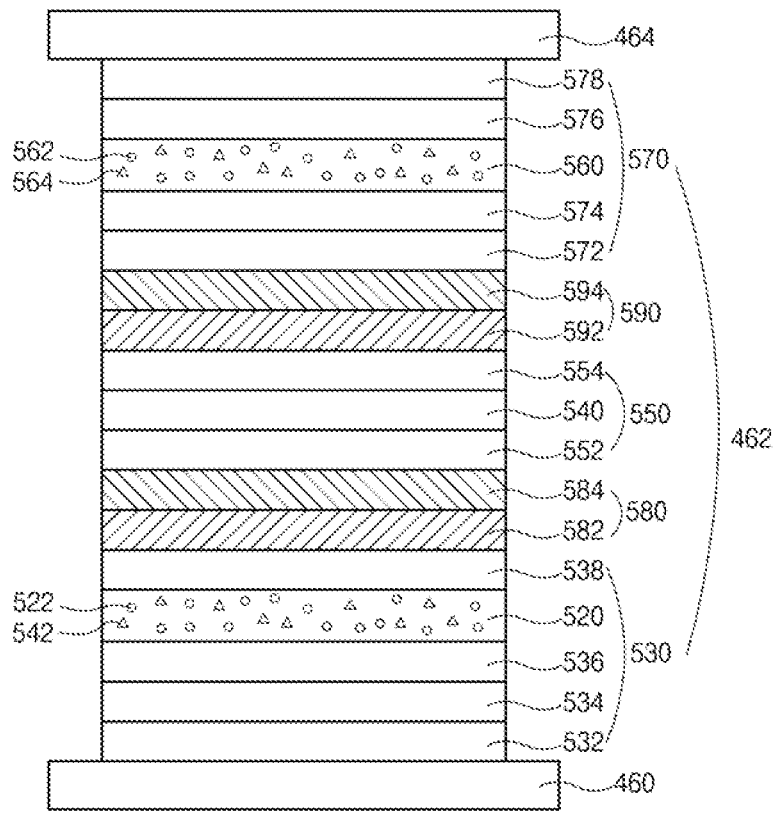
FIG. 7 is a schematic cross-sectional view illustrating an OLED having a tandem structure of three emitting parts for the organic light emitting display device according to the second embodiment of the present disclosure.

FIG. 5 is a schematic cross-sectional view illustrating an organic light emitting display device according to a second embodiment of the present disclosure, and FIG. 6 is a schematic cross-sectional view illustrating an OLED having a tandem structure of two emitting parts for the organic light emitting display device according to the second embodiment of the present disclosure. FIG. 7 is a schematic cross-sectional view illustrating an OLED having a tandem structure of three emitting parts for the organic light emitting display device according to the second embodiment of the present disclosure.

As shown in FIG. 5, the organic light emitting display device 400 includes a first substrate 410, where a red pixel RP, a green pixel GP and a blue pixel BP are defined, a second substrate 470 facing the first substrate 410, an OLED D, which is positioned between the first and second substrates 410 and 470 and providing white emission, and a color filter layer 480 between the OLED D and the second substrate 470.

Each of the first and second substrates 410 and 470 can be a glass substrate or a flexible substrate. For example, each of the first and second substrates 410 and 470 can be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 420 is formed on the substrate, and the TFT Tr corresponding to each of the red, green and blue pixels RP, GP and BP is formed on the buffer layer 420. The buffer layer 420 can be omitted.

A semiconductor layer 422 is formed on the buffer layer 420. The semiconductor layer 422 can include an oxide semiconductor material or polycrystalline silicon.

A gate insulating layer 424 is formed on the semiconductor layer 422. The gate insulating layer 424 can be formed of an inorganic insulating material such as silicon oxide or silicon nitride.

A gate electrode 430, which is formed of a conductive material, e.g., metal, is formed on the gate insulating layer 424 to correspond to a center of the semiconductor layer 422.

An interlayer insulating layer 432, which is formed of an insulating material, is formed on the gate electrode 430. The interlayer insulating layer 432 can be formed of an inorganic insulating material, e.g., silicon oxide or silicon nitride, or an organic insulating material, e.g., benzocyclobutene or photo-acryl.

The interlayer insulating layer 432 includes first and second contact holes 434 and 436 exposing both sides of the semiconductor layer 422. The first and second contact holes 434 and 436 are positioned at both sides of the gate electrode 430 to be spaced apart from the gate electrode 430.

A source electrode 440 and a drain electrode 442, which are formed of a conductive material, e.g., metal, are formed on the interlayer insulating layer 432.

The source electrode 440 and the drain electrode 442 are spaced apart from each other with respect to the gate electrode 430 and respectively contact both sides of the semiconductor layer 422 through the first and second contact holes 434 and 436.

The semiconductor layer 422, the gate electrode 430, the source electrode 440 and the drain electrode 442 constitute the TFT Tr. The TFT Tr serves as a driving element. Namely, the TFT Tr can correspond to the driving TFT Td (of FIG. 1).

The gate line and the data line cross each other to define the pixel, and the switching TFT is formed to be connected to the gate and data lines. The switching TFT is connected to the TFT Tr as the driving element.

In addition, the power line, which can be formed to be parallel to and spaced apart from one of the gate and data lines, and the storage capacitor for maintaining the voltage of the gate electrode of the TFT Tr in one frame can be further formed.

A passivation layer 450, which includes a drain contact hole 452 exposing the drain electrode 442 of the TFT Tr, is formed to cover the TFT Tr.

A first electrode 460, which is connected to the drain electrode 442 of the TFT Tr through the drain contact hole 452, is separately formed in each pixel and on the passivation layer 450. The first electrode 460 can be an anode and can be formed of a conductive material, e.g., a transparent conductive oxide (TCO), having a relatively high work function. For example, the first electrode 460 can be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 400 is operated in a bottom-emission type, the first electrode 460 can have a single-layered structure of the transparent conductive material layer. When the Organic light emitting display device 400 is operated in a top-emission type, a reflection electrode or a reflection layer can be formed under the first electrode 460. For example, the reflection electrode or the reflection layer can be formed of silver (Ag) or aluminum-palladium-copper (APC) alloy. In this instance, the first electrode 460 can have a triple-layered structure of ITO/Ag/ITO or ITO/APC/ITO.

A bank layer 466 is formed on the passivation layer 450 to cover an edge of the first electrode 460. Namely, the bank layer 466 is positioned at a boundary of the pixel and exposes a center of the first electrode 460 in the pixel. Since the OLED D emits the white light in the red, green and blue pixels RP, GP and BP, the organic emitting layer 462 can be formed as a common layer in the red, green and blue pixels RP, GP and BP without separation. The bank layer 466 can be formed to prevent a current leakage at an edge of the first electrode 460 and can be omitted.

An organic emitting layer 462 is formed on the first electrode 460.

Referring to FIG. 6, the OLED D includes the first and second electrodes 460 and 464 facing each other and the organic emitting layer 462 between the first and second electrodes 460 and 464. The organic emitting layer 462 includes a first emitting part 710 including a first EML 720, a second emitting part 730 including a second EML 740 and a charge generation layer (CGL) 750 between the first and second emitting parts 710 and 730.

The first electrode 460 can be formed of a conductive material having a relatively high work function to serve as an anode for injecting a hole into the organic emitting layer 462. The second electrode 464 can be formed of a conductive material having a relatively low work function to serve as a cathode for injecting an electron into the organic emitting layer 462.

The CGL 750 is positioned between the first and second emitting parts 710 and 730, and the first emitting part 710, the CGL 750 and the second emitting part 730 are sequentially stacked on the first electrode 460. Namely, the first emitting part 710 is positioned between the first electrode 460 and the CGL 750, and the second emitting part 730 is positioned between the second electrode 464 and the CGL 750.

The first emitting part 710 includes a first EML 720. In addition, the first emitting part 710 can further include a first EBL 716 between the first electrode 460 and the first EML 720 and a first HBL 718 between the first EML 720 and the CGL 750.

In addition, the first emitting part 710 can further include a first HTL 714 between the first electrode 460 and the first EBL 716 and an HIL 712 between the first electrode 460 and the first HTL 714.

The first EML 720 includes the emitting compound in Formula 1 as a first compound 722 and provides blue emission. For example, the first compound 722 in the first EML 720 can be one of the compounds in Formula 3.

The EML 720 can further include a second compound 724. For example, the second compound 724 can be represented by Formula 4 and can be one of the compounds in Formula 5.

In the first EML 720, the first compound 722 has a weight % being smaller than the second compound 724. The first compound 722 can act as a dopant (an emitter), and the second compound 724 can act as a host. For example, in the first EML 720, the first compound 722 can have a weight % of about 0.1 weight % to 30 weight %. To provide sufficient emitting efficiency and lifespan, the weight % of the first compound 722 can be about 0.1 weight % to 10 weight %, preferably about 1 weight % to 5 weight %.

The first EBL 716 can include the compound in Formula 6 as the electron blocking material. In addition, the first HBL 718 can include at least one of the compounds in Formula 8 and Formula 10 as the hole blocking material.

The second emitting part 730 includes the second EML 740. In addition, the second emitting part 730 can further include a second EBL 734 between the CGL 750 and the second EML 740 and a second HBL 736 between the second EML 740 and the second electrode 464.

In addition, the second emitting part 730 can further include a second HTL 732 between the CGL 750 and the second EBL 734 and an EIL 738 between the second HBL 736 and the second electrode 464.

The second EML 740 can be a yellow-green EML. For example, the second EML 740 can include a yellow-green dopant 743 and a host 745. The yellow-green dopant 743 can be one of a yellow-green fluorescent compound, a yellow-green phosphorescent compound and a yellow-green delayed fluorescent compound.

In the second EML 740, the host 745 can have a weight % of about 70 weight % to 99.9 weight %, and the yellow-green dopant 743 can have a weight % of about 0.1 weight % to 30 weight %. To provide sufficient emitting efficiency, the yellow-green dopant 743 can have a weight % of about 0.1 weight % to 10 weight %, preferably about 1 weight % to 5 weight %.

The second EBL 734 can include the compound in Formula 6 as the electron blocking material. In addition, the second HBL 736 can include at least one of the compounds in Formula 8 and Formula 10 as the hole blocking material.

The CGL 750 is positioned between the first and second emitting parts 710 and 730. Namely, the first and second emitting parts 710 and 730 are connected through the CGL 750. The CGL 750 can be a P-N junction CGL of an N-type CGL 752 and a P-type CGL 754.

The N-type CGL 752 is positioned between the first HBL 718 and the second HTL 732, and the P-type CGL 754 is positioned between the N-type CGL 752 and the second HTL 732.

In FIG. 6, the first EML 720, which is positioned between the first electrode 460 and the CGL 750, includes the first compound 722 being the emitting compound of the present disclosure and the second compound 724 being the anthracene derivative, and the second EML 740, which is positioned between the second electrode 464 and the CGL 750, is the yellow-green EML. Alternatively, the first EML 720, which is positioned between the first electrode 460 and the CGL 750, can be the yellow-green EML, and the second EML 740, which is positioned between the second electrode 464 and the CGL 750, can include the emitting compound of the present disclosure and the anthracene derivative to be a blue EML.

In the OLED D, since the first EML 720 or the second EML 740 includes the emitting compound 722 of the present disclosure such that the emitting efficiency and the lifespan of the OLED D and the organic light emitting display device 400 are significantly improved.

The OLED D including the first emitting part 710 providing the blue emission and the second emitting part 730 providing the yellow-green emission, emits a white light.

Referring to FIG. 7, the organic emitting layer 462 includes a first emitting part 530 including a first EML 520, a second emitting part 550 including a second EML 540, a third emitting part 570 including a third EML 560, a first CGL 580 between the first and second emitting parts 530 and 550 and a second CGL 590 between the second and third emitting parts 550 and 570.

The first CGL 580 is positioned between the first and second emitting parts 530 and 550, and the second CGL 590 is positioned between the second and third emitting parts 550 and 570. Namely, the first emitting part 530, the first CGL 580, the second emitting part 550, the second CGL 590 and the third emitting part 570 are sequentially stacked on the first electrode 460. In other words, the first emitting part 530 is positioned between the first electrode 460 and the first CGL 580, the second emitting part 550 is positioned between the first and second CGLs 580 and 590, and the third emitting part 570 is positioned between the second electrode 464 and the second CGL 590.

The first emitting part 530 can include an HIL 532, a first HTL 534, a first EBL 536, the first EML 520 and a first HBL 538 sequentially stacked on the first electrode 460. For example, the HIL 532, the first HTL 534 and the first EBL 536 are positioned between the first electrode 460 and the first EML 520, and the first HBL 538 is positioned between the first EML 520 and the first CGL 580.

The first EML 520 includes the emitting compound in Formula 1 as a first compound 522 and provides blue emission. For example, the first compound 522 in the first EML 520 can be one of the compounds in Formula 3.

The EML 520 can further include a second compound 542. For example, the second compound 542 can be represented by Formula 4 and can be one of the compounds in Formula 5.

In the first EML 520, the first compound 522 has a weight % being smaller than the second compound 542. The first compound 522 can act as a dopant (an emitter), and the second compound 542 can act as a host. For example, in the first EML 520, the first compound 522 can have a weight % of about 0.1 weight % to 30 weight %. To provide sufficient emitting efficiency and lifespan, the weight % of the first compound 522 can be about 0.1 weight % to 10 weight %, preferably about 1 weight % to 5 weight %.

The first EBL 536 can include the compound in Formula 6 as the electron blocking material. In addition, the first HBL 538 can include at least one of the compounds in Formula 8 and Formula 10 as the hole blocking material.

The second emitting part 550 can include a second HTL 552, the second EML 540 and an electron transporting layer (ETL) 554. The second HTL 552 is positioned between the first CGL 580 and the second EML 540, and the ETL 554 is positioned between the second EML 540 and the second CGL 590.

The second EML 540 can be a yellow-green EML. For example, the second EML 540 can include a host and a yellow-green dopant.

Alternatively, the second EML 540 can include a host, a red dopant and a green dopant. In this instance, the second EML 540 can have a single-layered structure or a double-layered structure of a lower layer including the host and the red dopant (or the green dopant) and an upper layer including the host and the green dopant (or the red dopant).

The second EML 540 can have a triple-layered structure of a first layer, which includes a host and a red dopant, a second layer, which includes a host and a yellow-green dopant, and a third layer, which includes a host and a green dopant.

The third emitting part 570 can include a third HTL 572, a second EBL 574, the third EML 560, a second HBL 576 and an EIL 578.

The third EML 560 includes the emitting compound in Formula 1 as a third compound 562 and provides blue emission. For example, the third compound 562 in the third EML 560 can be one of the compounds in Formula 3.

The third EML 560 can further include a fourth compound 564. For example, the fourth compound 564 can be represented by Formula 4 and can be one of the compounds in Formula 5.

In the third EML 560, the third compound 562 can have a weight % being less than the fourth compound 564. In the third EML 560, the third compound 562 can act as a dopant (an emitter), and the fourth compound 564 can act as a host. For example, in the third EML 560, the third compound 562 has a weight % of about 0.1 weight % to 30 weight %. To provide sufficient emitting efficiency and lifespan, the weight % of the third compound 562 can be about 0.1 weight % to 10 weight %, preferably about 1 weight % to 5 weight %.

The third compound 562 in the third EML 560 and the first compound 522 in the first EML 520 can be same or different, and the fourth compound 564 in the third EML 560 and the second compound 542 in the first EML 520 can be same or different. In addition, the weight % of the first compound 522 in the first EML 520 and the weight % of the third compound 562 in the third EML 560 can be same or different.

The second EBL 574 can include the electron blocking material in Formula 6. In addition, the second HBL 576 can include at least one of the hole blocking material in Formula 8 and the hole blocking material in Formula 10.

The first CGL 580 is positioned between the first emitting part 530 and the second emitting part 550, and the second CGL 590 is positioned between the second emitting part 550 and the third emitting part 570. Namely, the first and second emitting parts 530 and 550 are connected through the first CGL 580, and the second and third emitting parts 550 and 570 are connected through the second CGL 590. The first CGL 580 can be a P-N junction CGL of a first N-type CGL 582 and a first P-type CGL 584, and the second CGL 590 can be a P-N junction CGL of a second N-type CGL 592 and a second P-type CGL 594.

In the first CGL 580, the first N-type CGL 582 is positioned between the first HBL 538 and the second HTL 552, and the first P-type CGL 584 is positioned between the first N-type CGL 582 and the second HTL 552.

In the second CGL 590, the second N-type CGL 592 is positioned between the ETL 554 and the third HTL 572, and the second P-type CGL 594 is positioned between the second N-type CGL 592 and the third HTL 572.

In the OLED D, since each of the first and third EMLs 520 and 560 includes the emitting compound in Formula 1 as the first and third compounds 522 and 562, respectively, the emitting efficiency and the lifespan of the OLED D and the organic light emitting display device 400 are improved.

In addition, the OLED D including the first and third emitting parts 530 and 570 with the second emitting part 550, which emits yellow-green light or red/green light, can emit white light.

In FIG. 7, the OLED D has a triple-stack structure of the first, second and third emitting parts 530, 550 and 570. Alternatively, the OLED D can further include additional emitting part and CGL.

Referring to FIG. 5 again, a second electrode 464 is formed over the substrate 410 where the organic emitting layer 462 is formed.

In the organic light emitting display device 400, since the light emitted from the organic emitting layer 462 is incident to the color filter layer 480 through the second electrode 464, the second electrode 464 has a thin profile for transmitting the light.

The first electrode 460, the organic emitting layer 462 and the second electrode 464 constitute the OLED D.

The color filter layer 480 is positioned over the OLED D and includes a red color filter 482, a green color filter 484 and a blue color filter 486 respectively corresponding to the red, green and blue pixels RP, GP and BP. The red color filter 482 can include at least one of red dye and red pigment, the green color filter 484 can include at least one of green dye and green pigment, and the blue color filter 486 can include at least one of blue dye and blue pigment.

The color filter layer 480 can be attached to the OLED D by using an adhesive layer. Alternatively, the color filter layer 480 can be formed directly on the OLED D.

An encapsulation film can be formed to prevent penetration of moisture into the OLED D. For example, the encapsulation film can include a first inorganic insulating layer, an organic insulating layer and a second inorganic insulating layer sequentially stacked, but it is not limited thereto. The encapsulation film can be omitted.

A polarization plate for reducing an ambient light reflection can be disposed over the top-emission type OLED D. For example, the polarization plate can be a circular polarization plate.

In the OLED of FIG. 5, the first and second electrodes 460 and 464 are a reflection electrode and a transparent (or semi-transparent) electrode, respectively, and the color filter layer 480 is disposed over the OLED D. Alternatively, when the first and second electrodes 460 and 464 are a transparent (or semi-transparent) electrode and a reflection electrode, respectively, the color filter layer 480 can be disposed between the OLED D and the first substrate 410.

A color conversion layer can be formed between the OLED D and the color filter layer 480. The color conversion layer can include a red color conversion layer, a green color conversion layer and a blue color conversion layer respectively corresponding to the red, green and blue pixels RP, GP and BP. The white light from the OLED D is converted into the red light, the green light and the blue light by the red, green and blue color conversion layer, respectively. For example, the color conversion layer can include a quantum dot. Accordingly, the color purity of the organic light emitting display device 400 can be further improved.

The color conversion layer can be included instead of the color filter layer 480.

As described above, in the organic light emitting display device 400, the OLED D in the red, green and blue pixels RP, GP and BP emits the white light, and the white light from the organic light emitting diode D passes through the red color filter 482, the green color filter 484 and the blue color filter 486. As a result, the red light, the green light and the blue light are provided from the red pixel RP, the green pixel GP and the blue pixel BP, respectively.

In FIGS. 5 to 7, the OLED D emitting the white light is used for a display device. Alternatively, the OLED D can be formed on an entire surface of a substrate without at least one of the driving element and the color filter layer to be used for a lightening device. The display device and the lightening device each including the OLED D of the present disclosure can be referred to as an organic light emitting device.

Figure 8:
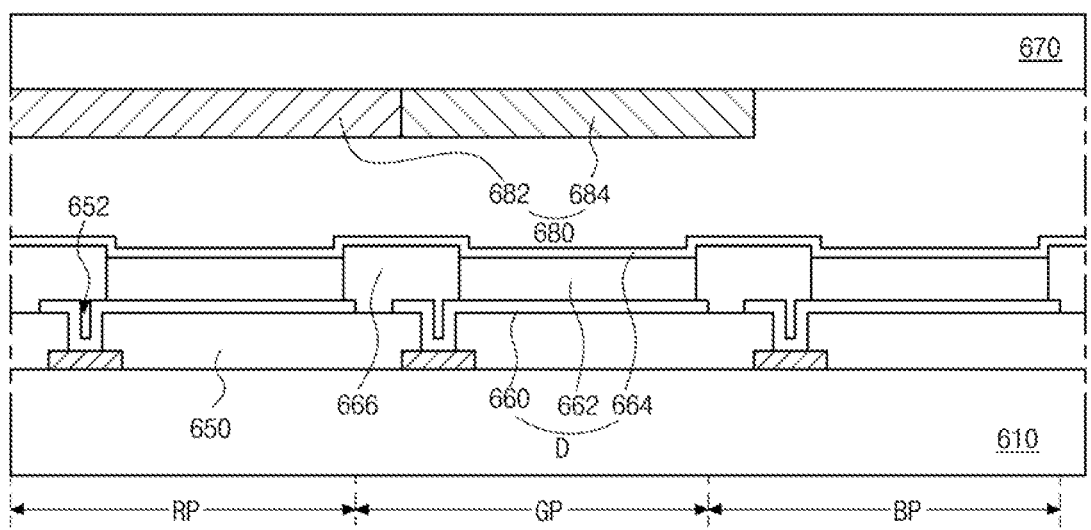
FIG. 8 is a schematic cross-sectional view illustrating an organic light emitting display device according to a third embodiment of the present disclosure.

FIG. 8 is a schematic cross-sectional view illustrating an organic light emitting display device according to a third embodiment of the present disclosure.

As shown in FIG. 8, the organic light emitting display device 600 includes a first substrate 610, where a red pixel RP, a green pixel GP and a blue pixel BP are defined, a second substrate 670 facing the first substrate 610, an OLED D, which is positioned between the first and second substrates 610 and 670 and providing white emission, and a color conversion layer 680 between the OLED D and the second substrate 670.

A color filter can be formed between the second substrate 670 and each color conversion layer 680.

Each of the first and second substrates 610 and 670 can be a glass substrate or a flexible substrate. For example, each of the first and second substrates 610 and 670 can be a polyimide (PI) substrate, a polyethersulfone (PES) substrate, a polyethylenenaphthalate (PEN) substrate, a polyethylene terephthalate (PET) substrate or a polycarbonate (PC) substrate.

A TFT Tr, which corresponding to each of the red, green and blue pixels RP, GP and BP, is formed on the first substrate 610, and a passivation layer 650, which has a drain contact hole 652 exposing an electrode, e.g., a drain electrode, of the TFT Tr is formed to cover the TFT Tr.

The OLED D including a first electrode 660, an organic emitting layer 662 and a second electrode 664 is formed on the passivation layer 650. In this instance, the first electrode 660 can be connected to the drain electrode of the TFT Tr through the drain contact hole 652.

A bank layer 666 is formed on the passivation layer 650 to cover an edge of the first electrode 660. Namely, the bank layer 666 is positioned at a boundary of the pixel and exposes a center of the first electrode 660 in the pixel. Since the OLED D emits the blue light in the red, green and blue pixels RP, GP and BP, the organic emitting layer 662 can be formed as a common layer in the red, green and blue pixels RP, GP and BP without separation. The bank layer 666 can be formed to prevent a current leakage at an edge of the first electrode 660 and can be omitted.

The OLED D emits a blue light and can have a structure shown in FIG. 3 or FIG. 4. Namely, the OLED D is formed in each of the red, green and blue pixels RP, GP and BP and provides the blue light.

The color conversion layer 680 includes a first color conversion layer 682 corresponding to the red pixel RP and a second color conversion layer 684 corresponding to the green pixel GP. For example, the color conversion layer 680 can include an inorganic color conversion material such as a quantum dot. The color conversion layer 680 is not presented in the blue pixel BP such that the OLED D in the blue pixel BP can directly face the second substrate 670.

The blue light from the OLED D is converted into the red light by the first color conversion layer 682 in the red pixel RP, and the blue light from the OLED D is converted into the green light by the second color conversion layer 684 in the green pixel GP.

Accordingly, the organic light emitting display device 600 can display a full-color image.

On the other hand, when the light from the OLED D passes through the first substrate 610, the color conversion layer 680 is disposed between the OLED D and the first substrate 610.

It will be apparent to those skilled in the art that various modifications and variations can be made in the embodiments of the present disclosure without departing from the spirit or scope of the present disclosure. Thus, it is intended that the modifications and variations cover this disclosure provided they come within the scope of the appended claims and their equivalents.

What is claimed is:

1. An emitting compound represented by Formula 2-2 or Formula 2-4:

[Formula 2-2]

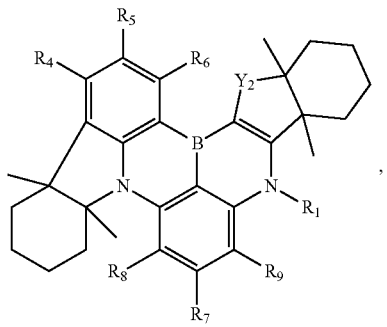

wherein $R_1$ is selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, and $Y_2$ is O or S, each of $R_4$ to $R_6$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, and each of $R_7$, $R_8$, and $R_9$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl; and

[Formula 2-4]

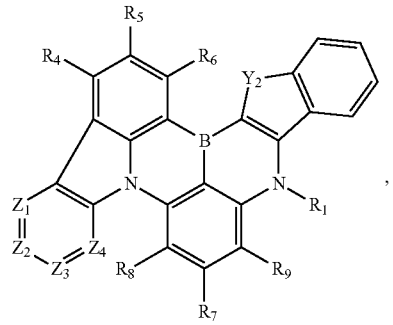

wherein $R_1$ is selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, $Y_2$ is O or S, each of $R_4$ to $R_6$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, each of $Z_1$ to $Z_4$ is independently N or $CR_{10}$, and at least one of $Z_1$ to $Z_4$ is N, wherein each of $R_7$ to $R_{10}$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl.

2. The emitting compound according to claim 1, wherein the emitting compound of Formula 2-2 or Formula 2-4 is one of the compounds in Formula 3:

[Formula 3]
1-1
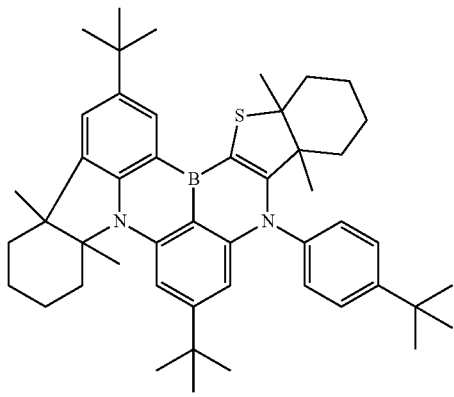
1-2
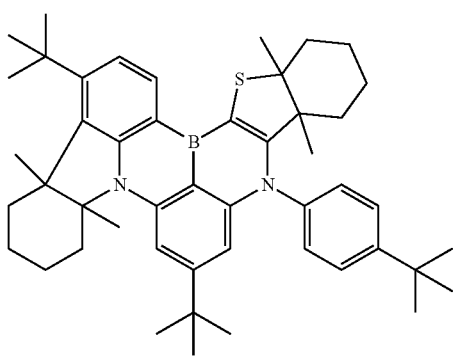
1-3
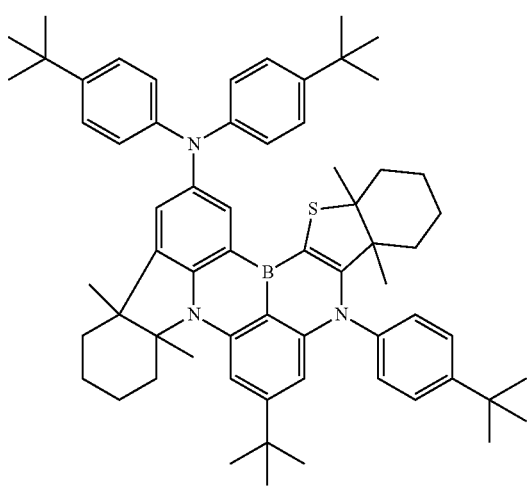
1-4
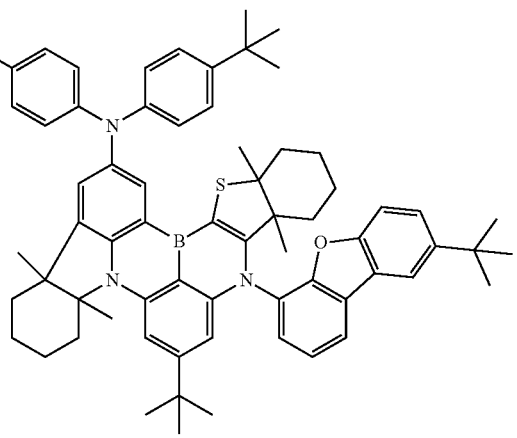
1-5
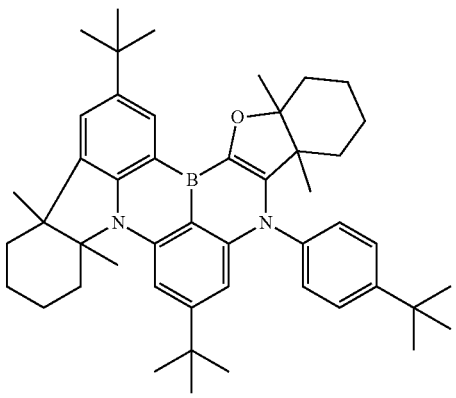
1-6
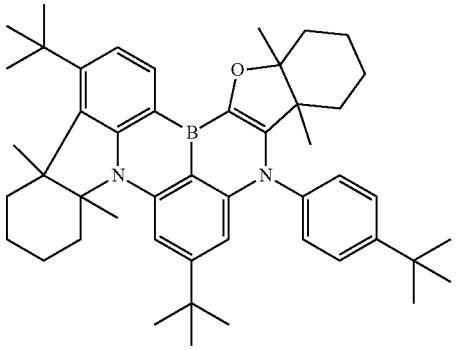

1-7
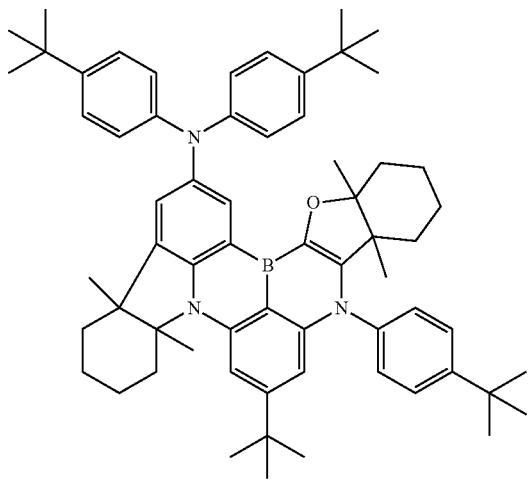
1-8
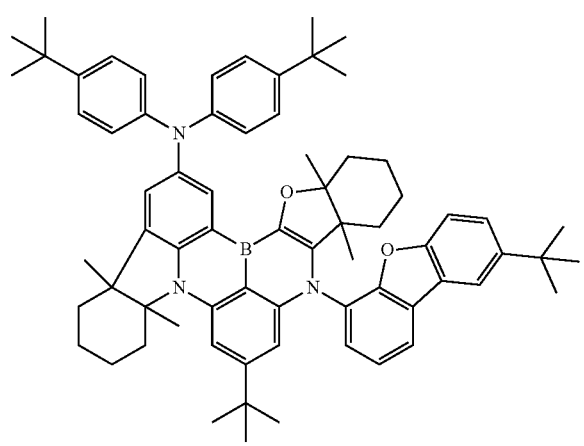
2-1
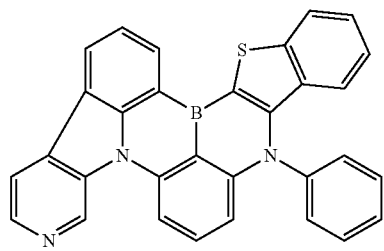
2-2
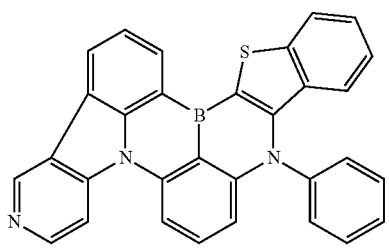
2-3
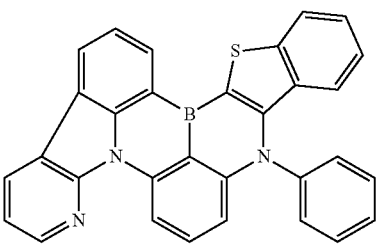
2-4
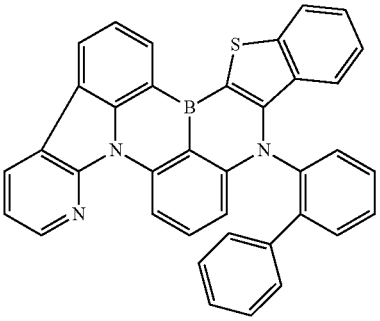
2-5
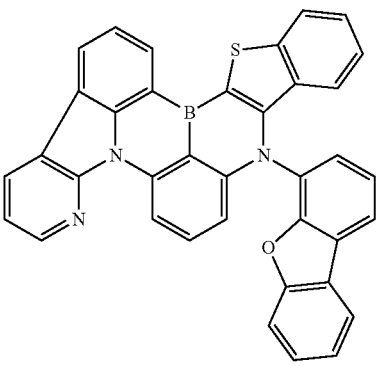
2-6
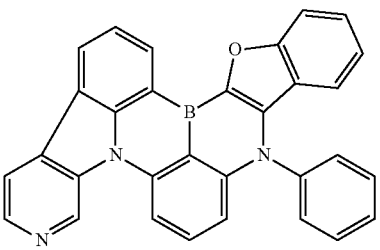
2-7
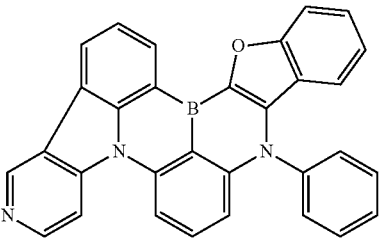

-continued

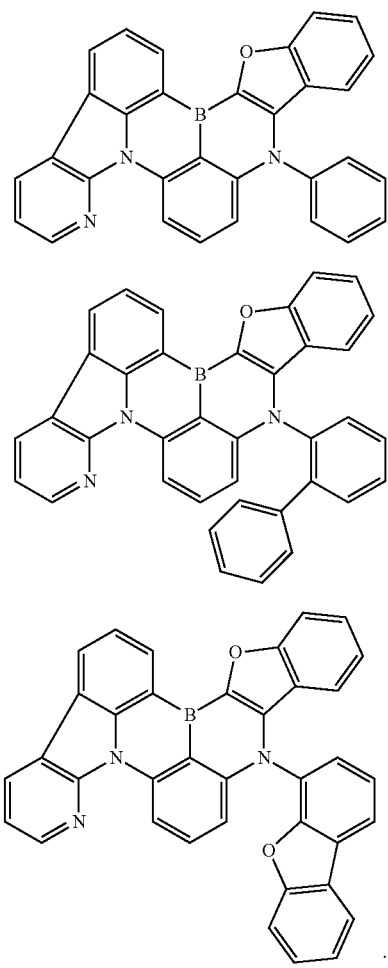

2-8

2-9

2-10

3. An organic light emitting device, comprising:
a substrate; and
an organic light emitting diode positioned on the substrate and including a first electrode; a second electrode facing the first electrode; and a first emitting material layer including a first compound and positioned between the first and second electrodes,
wherein the first compound is the emitting compound represented by Formula 2-2 or Formula 2-4 of claim 1.

4. The organic light emitting device of claim 3, wherein the first emitting material layer further includes a second compound,
wherein the second compound is represented by Formula 4:

[Formula 4]

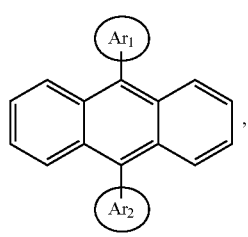

wherein each of $Ar_1$ and $Ar_2$ is independently C6 to C30 aryl group or C5 to C30 heteroaryl group, L is a single bond or C6 to C30 arylene group, and
wherein hydrogens in the second compound are not deuterated or partially or wholly deuterated.

5. The organic light emitting device of claim 4, wherein the second compound is one of the compounds in Formula 5:

[Formula 5]

H-1

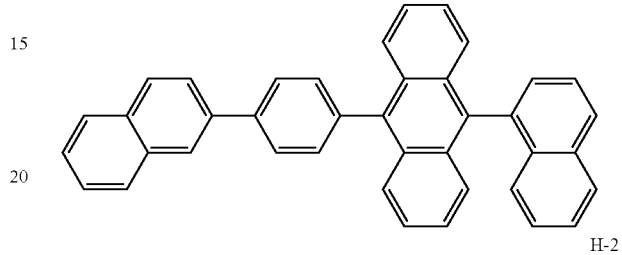

H-2

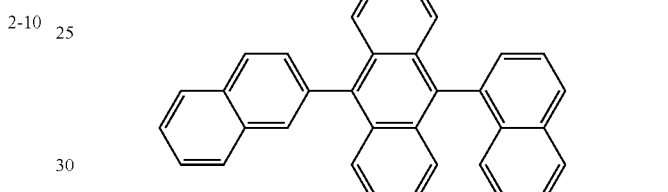

H-3

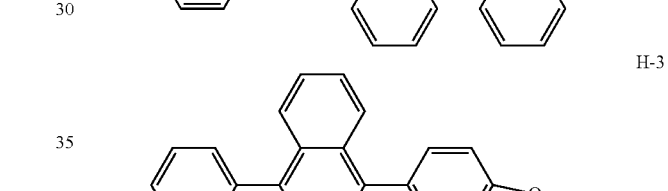

H-4

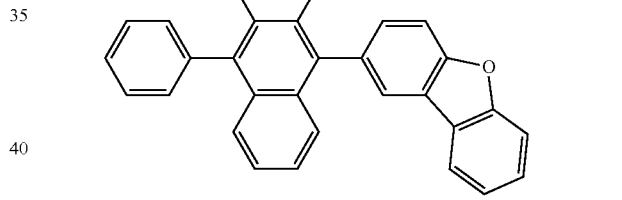

H-5

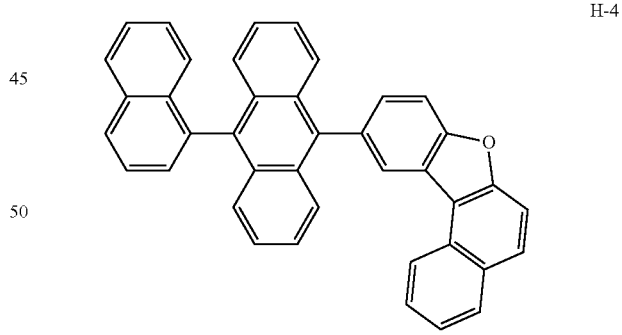

-continued

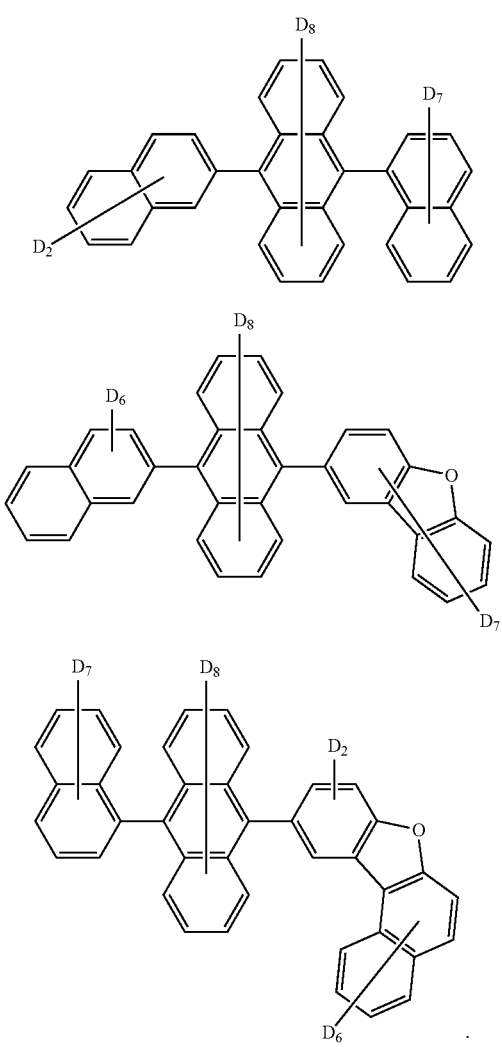

6. The organic light emitting device of claim 3, wherein the organic light emitting diode further includes:
a second emitting material layer including a third compound and positioned between the first emitting material layer and the second electrode; and
a first charge generation layer between the first and second emitting material layers, and
wherein the third compound is the emitting compound of Formula 2-2 or Formula 2-4.

7. The organic light emitting device of claim 3, wherein a red pixel, a green pixel and a blue pixel are defined on the substrate, and the organic light emitting diode corresponds to each of the red, green and blue pixels, and
wherein the organic light emitting device further includes:
a color conversion layer disposed between the substrate and the organic light emitting diode or on the organic light emitting diode and corresponding to the red and green pixels.

8. The organic light emitting device of claim 6, wherein the organic light emitting diode further includes:
a third emitting material layer positioned between the first charge generation layer and the second emitting material layer; and
a second charge generation layer between the second and third emitting material layers, and wherein the third emitting material layer emits a yellow-green light or red and green lights.

9. The organic light emitting device of claim 3, wherein the organic light emitting diode further includes:
a second emitting material layer emitting a yellow-green light and positioned between the first emitting material layer and the second electrode; and
a charge generation layer between the first and second emitting material layers.

10. The organic light emitting device of claim 3, wherein a red pixel, a green pixel and a blue pixel are defined on the substrate, and the organic light emitting diode corresponds to each of the red, green and blue pixels, and
wherein the organic light emitting device further includes:
a color filter layer disposed between the substrate and the organic light emitting diode or on the organic light emitting diode and corresponding to the red, green and blue pixels.

11. The organic light emitting device according to claim 3, wherein the first compound is represented by Formula 2-2:

[Formula 2-2]

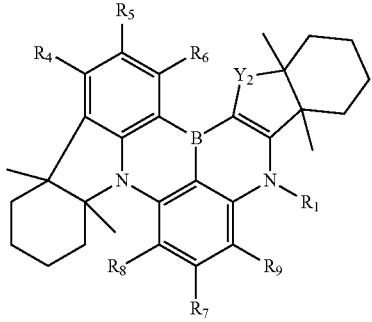

wherein $R_1$ is selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl,
$Y_2$ is O or S,
each of $R_4$ to $R_6$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, and
wherein each of $R_7$ to $R_9$ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl.

12. The organic light emitting device according to claim 3, wherein the first compound is represented by Formula 2-4:

[Formula 2-4]

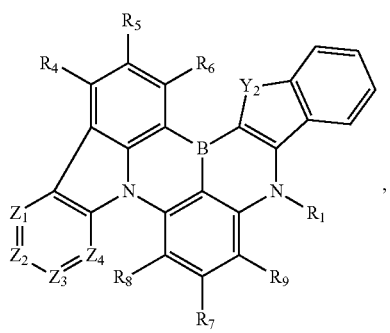

wherein R₁ is selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl, and wherein Y₂ is O or S, wherein each of Z₁ to Z₄ is independently N or CR₁₀, and at least one of Z₁ to Z₄ is N, and wherein each of R₄ to R₆ is independently selected from the group consisting of hydrogen, deuterium, C1 to C10 alkyl group unsubstituted or substituted with deuterium, C6 to C30 arylamine group unsubstituted or substituted with deuterium or C1 to C10 alkyl, C6 to C30 aryl group unsubstituted or substituted with deuterium or C1 to C10 alkyl, and C5 to C30 heteroaryl group unsubstituted or substituted with deuterium or C1 to C10 alkyl.

13. The organic light emitting device according to claim 3, wherein the first compound is one of the compounds in Formula 3:

[Formula 3]

1-1

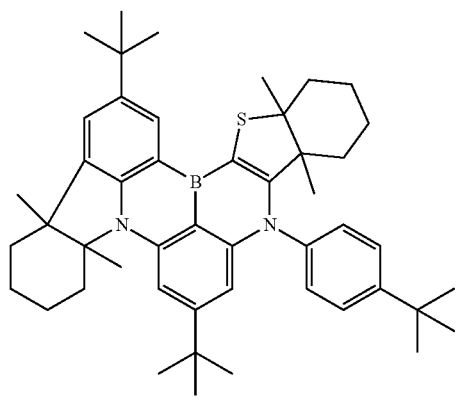

1-2

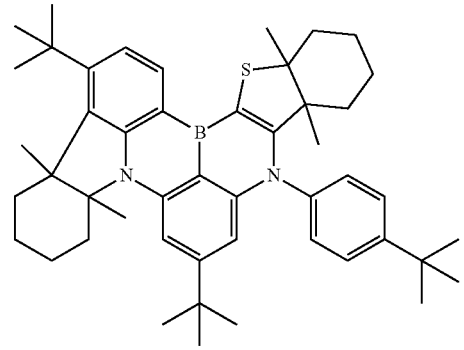

1-3

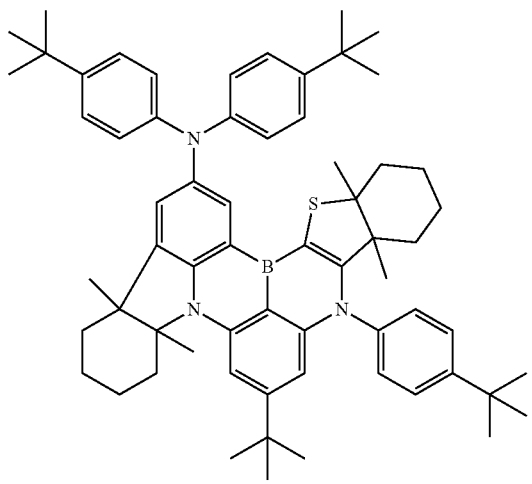

1-4

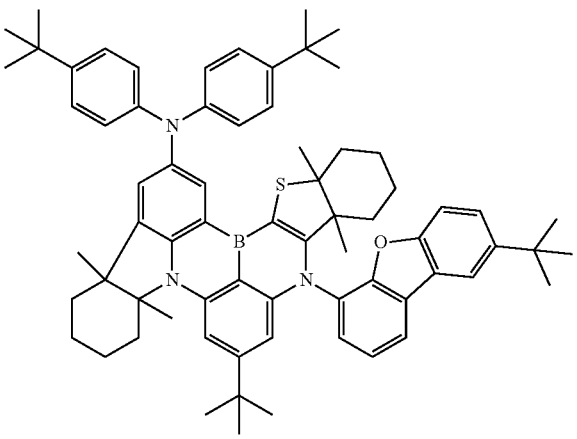

-continued
1-5
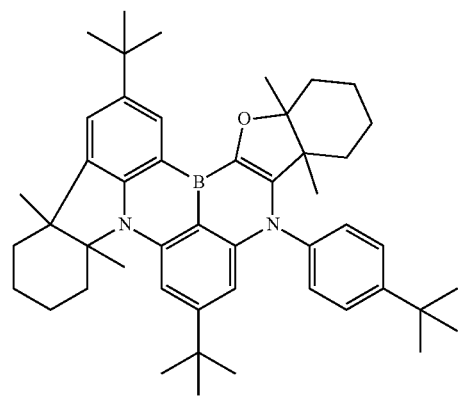
1-6
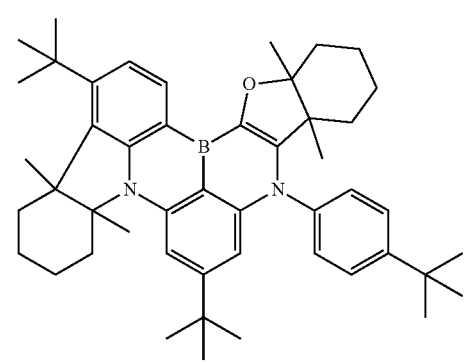
1-7
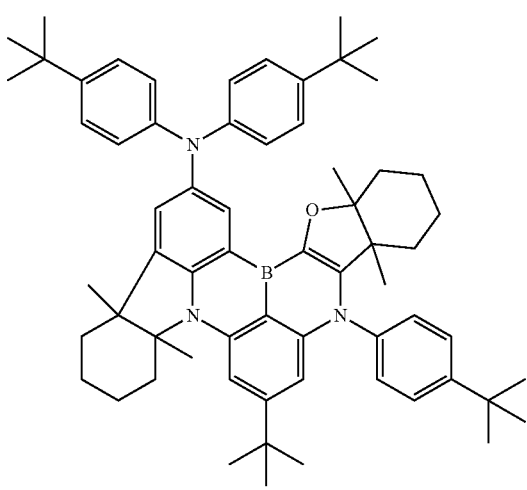
-continued
1-8
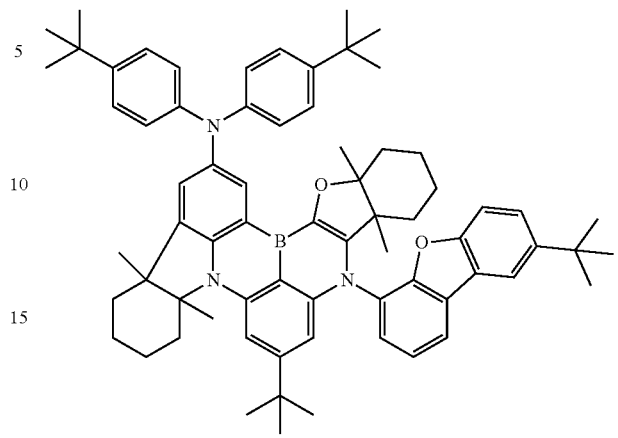
2-1
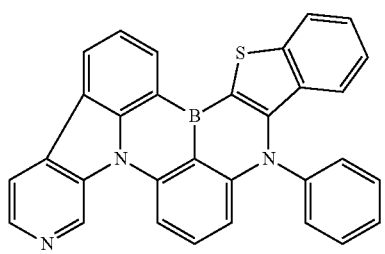
2-2
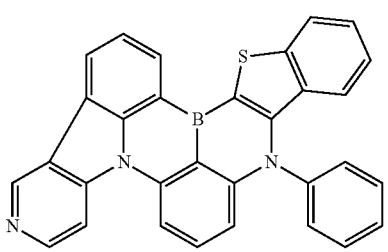
2-3
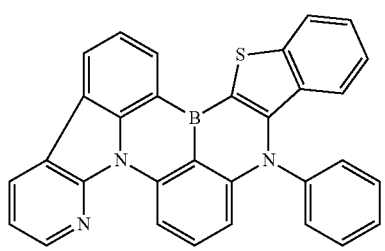
2-4
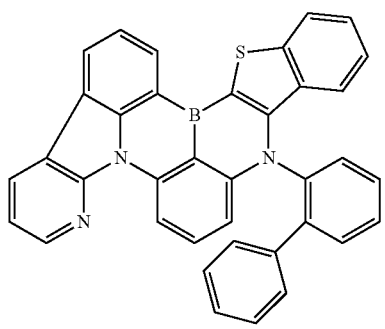

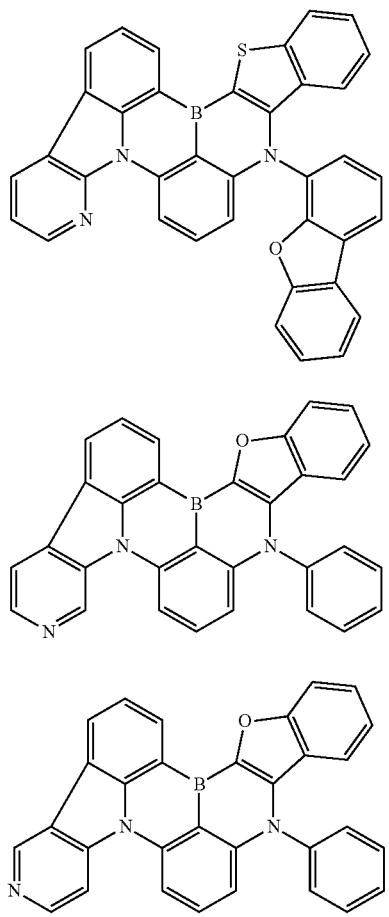
2-5
2-6
2-7
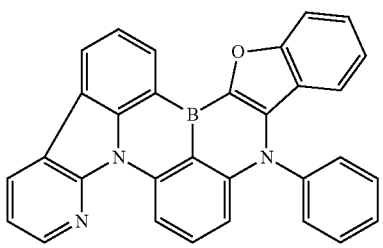
2-8
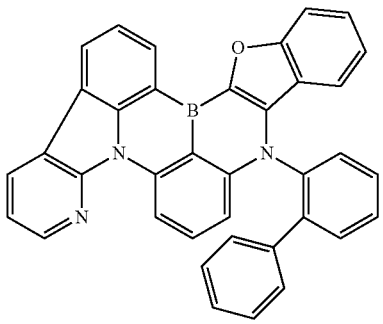
2-9
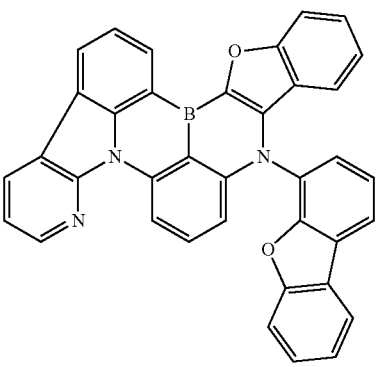
2-10
* * * * *